(12) United States Patent
Tabor et al.

(10) Patent No.: US 9,896,540 B2
(45) Date of Patent: *Feb. 20, 2018

(54) POLYESTER POLYOLS FROM RECYCLED POLYMERS AND WASTE STREAMS

(71) Applicant: Resinate Materials Group, Inc., Plymouth, MI (US)

(72) Inventors: Rick Tabor, Plymouth, MI (US); Eric David Vrabel, Ferndale, MI (US); Matthew J Beatty, Ann Arbor, MI (US); Gary E. Spilman, Northville, MI (US); Kevin Anthony Rogers, Farmington, MI (US); Michael Robert Christy, Howell, MI (US); Matthew Thomas Brown, Novi, MI (US); Jack Rogers Kovsky, Detroit, MI (US); Woo-Sung Bae, Midland, MI (US); Shakti L Mukerjee, Canton, MI (US)

(73) Assignee: Resinate Materials Group, Inc., Plymouth, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/205,235

(22) Filed: Jul. 8, 2016

(65) Prior Publication Data

US 2017/0029561 A1 Feb. 2, 2017

Related U.S. Application Data

(63) Continuation of application No. PCT/US2015/045792, filed on Aug. 19, 2015.
(Continued)

(51) Int. Cl.

| | |
|---|---|
| *C08G 63/91* | (2006.01) |
| *C08J 9/14* | (2006.01) |
| *C08G 18/76* | (2006.01) |
| *C09D 5/03* | (2006.01) |
| *C08G 18/42* | (2006.01) |
| *C08F 20/10* | (2006.01) |
| *C09D 175/06* | (2006.01) |
| *C08G 18/28* | (2006.01) |
| *C07C 29/09* | (2006.01) |
| *C07C 31/18* | (2006.01) |
| *C08G 18/08* | (2006.01) |
| *C08J 11/24* | (2006.01) |
| *C09D 175/04* | (2006.01) |
| *C08G 18/66* | (2006.01) |
| *C08G 18/72* | (2006.01) |

(Continued)

(52) U.S. Cl.
CPC ............ *C08G 63/916* (2013.01); *C07C 29/09* (2013.01); *C07C 31/18* (2013.01); *C08F 20/10* (2013.01); *C08G 18/14* (2013.01); *C08G 18/28* (2013.01); *C08G 18/4213* (2013.01); *C08G 18/664* (2013.01); *C08G 18/722* (2013.01); *C08G 18/7671* (2013.01); *C08G 63/183* (2013.01); *C08J 9/141* (2013.01); *C08J 11/24* (2013.01); *C09D 5/03* (2013.01); *C09D 175/04* (2013.01); *C09D 175/06* (2013.01); *C08G 2101/00* (2013.01); *C08G 2101/0025* (2013.01); *C08G 2150/20* (2013.01); *C08J 2203/14* (2013.01); *C08J 2205/10* (2013.01); *C08J 2367/02* (2013.01); *C08J 2375/04* (2013.01); *Y02W 30/706* (2015.05)

(58) Field of Classification Search
CPC .............. C08G 63/916; C08G 18/7671; C08G 18/4213; C08G 63/183; C08G 2150/20; C08G 2101/0025; C08G 18/664; C08G 18/722; C08G 2101/00; C08G 8/28; C08G 18/14; C09D 5/03; C09D 175/06; C09D 175/04; C08F 20/10; C08J 11/24; C08J 2375/04; C08J 2203/14; C08J 2205/10; C08J 2367/02; C08J 9/141; Y02W 30/706; C07C 29/09; C07C 31/18
See application file for complete search history.

(56) References Cited

U.S. PATENT DOCUMENTS

| | | |
|---|---|---|
| 4,197,353 A | 4/1980 | Tobias et al. |
| 4,226,027 A | 10/1980 | Albus |

(Continued)

FOREIGN PATENT DOCUMENTS

| | | |
|---|---|---|
| CA | 2216772 | 4/1998 |
| CN | 102516593 | 6/2012 |

(Continued)

OTHER PUBLICATIONS

Martelli, et al. "Chicken feather keratin films plasticized with polyethylene glycol" Int. Jour. Poly. Mat Poly. Biomat. (2012), vol. 61, 1, pp. 17-29.

(Continued)

*Primary Examiner* — Rabon Sergent
(74) *Attorney, Agent, or Firm* — Dilworth IP LLC

(57) ABSTRACT

The present invention relates to polyester polyols made from aromatic polyacid sources such as thermoplastic polyesters. The polyols can be made by heating a thermoplastic polyester such as virgin polyethylene terephthalate, recycled polyethylene terephthalate, or mixtures thereof, with a glycol to give a digested intermediate which is then reacted with a digestible polymer, which can be obtained from various recycle waste streams. The polyester polyols comprise a glycol-digested polyacid source and a further digestible polymer. The polyester polyols provide a sustainable alternative to petrochemical or biochemical based polyester polyols.

27 Claims, No Drawings

Related U.S. Application Data

(60) Provisional application No. 62/039,816, filed on Aug. 20, 2014, provisional application No. 62/039,820, filed on Aug. 20, 2014, provisional application No. 62/082,974, filed on Nov. 21, 2014, provisional application No. 62/110,343, filed on Jan. 30, 2015, provisional application No. 62/110,347, filed on Jan. 30, 2015, provisional application No. 62/185,008, filed on Jun. 26, 2015.

(51) Int. Cl.
*C08G 63/183* (2006.01)
*C08G 101/00* (2006.01)

(56) References Cited

U.S. PATENT DOCUMENTS

| | | | |
|---|---|---|---|
| 4,520,139 | A | 5/1985 | Crehan et al. |
| 4,873,268 | A | 10/1989 | Hallmark et al. |
| 4,876,304 | A | 10/1989 | Mertz et al. |
| 5,068,395 | A * | 11/1991 | Bathe ............ C08G 63/48 524/311 |
| 5,147,926 | A | 9/1992 | Meichsner et al. |
| 5,294,729 | A | 3/1994 | Wicks et al. |
| 5,319,128 | A | 6/1994 | DuPont et al. |
| 5,420,166 | A * | 5/1995 | Tufts ............ C08J 11/06 521/40.5 |
| 5,612,467 | A | 3/1997 | Weuthen et al. |
| 5,637,654 | A | 6/1997 | Panandiker et al. |
| 5,763,692 | A | 6/1998 | Kierkus et al. |
| 5,922,474 | A | 7/1999 | Kuo |
| 5,968,992 | A | 10/1999 | Naber et al. |
| 6,069,182 | A | 5/2000 | Naber et al. |
| 6,750,260 | B2 | 6/2004 | Sendijarevic |
| 7,030,057 | B2 | 4/2006 | Matsumoto |
| 7,659,320 | B2 | 2/2010 | Berard |
| 7,902,264 | B2 | 3/2011 | Determan et al. |
| 8,344,172 | B2 | 1/2013 | Tabor et al. |
| 8,546,519 | B2 | 10/2013 | Selifonov |
| 8,604,077 | B2 | 12/2013 | Wicks et al. |
| 8,680,227 | B1 | 3/2014 | Bell et al. |
| 8,692,013 | B2 | 4/2014 | Tabor et al. |
| 2004/0102533 | A1 | 5/2004 | Durand et al. |
| 2006/0025544 | A1 | 2/2006 | Koube et al. |
| 2006/0089453 | A1 | 4/2006 | Pajerski |
| 2007/0225473 | A1 | 9/2007 | Determan et al. |
| 2008/0194713 | A1 | 8/2008 | Kim et al. |
| 2009/0131625 | A1 | 5/2009 | Kurian et al. |
| 2009/0234034 | A1 | 9/2009 | Blanco |
| 2010/0204392 | A1 | 8/2010 | Marsh et al. |
| 2011/0039959 | A1 | 2/2011 | Kim et al. |
| 2012/0035376 | A1 | 2/2012 | Mullen et al. |
| 2012/0118201 | A1 | 5/2012 | Mullen et al. |
| 2012/0121911 | A1 | 5/2012 | Mullen et al. |
| 2012/0190800 | A1 * | 7/2012 | Felice ............ C08G 63/183 525/419 |
| 2013/0072628 | A1 | 3/2013 | Crawford et al. |
| 2014/0060383 | A1 | 3/2014 | Wu et al. |
| 2014/0163127 | A1 | 6/2014 | Selifonov et al. |

FOREIGN PATENT DOCUMENTS

| | | |
|---|---|---|
| CN | 103030796 | 4/2013 |
| CN | 102061009 | 10/2013 |
| EP | 1693409 | 8/2006 |
| EP | 25652261 | 3/2013 |
| ES | 2277554 | 7/2008 |
| JP | 04189881 | 7/1992 |
| JP | 2000198876 | 7/2000 |
| JP | 2004161666 | 6/2004 |
| JP | 2004168811 | 6/2004 |
| JP | 2004168812 | 6/2004 |
| JP | 2004238581 | 8/2004 |
| JP | 2005002161 | 1/2005 |
| PL | 212329 | 9/2012 |
| WO | 2004005365 | 1/2004 |
| WO | 2007062118 | 5/2007 |
| WO | 2008085397 | 7/2008 |
| WO | 2009032905 | 3/2009 |
| WO | 2009048874 | 4/2009 |
| WO | 2009049041 | 4/2009 |
| WO | 2010075330 | 7/2010 |
| WO | 2010151558 | 12/2010 |
| WO | 2011138432 | 11/2011 |
| WO | 2012065116 | 5/2012 |
| WO | 2013154874 | 10/2013 |
| WO | 2014023684 | 2/2014 |
| WO | 2014027104 | 2/2014 |
| WO | 2014075051 | 5/2014 |

OTHER PUBLICATIONS

Wang et al. "A high-capacity carbon prepared from renewable chicken feather biopolymer for supercapacitors" Journ. Power Sources (2013) vol. 225, pp. 101-107.
Flores-Hernandez et al. "All green composites from fully renewable biopolymers: Chitosan-starch reinforced with keratin from feathers" Polymers (2014), vol. 6, No. 3 pp. 686-705.
Kim et al. "Kinetics of Polycarbonate Glycolysis in Ethylene Glycol", Ind. Eng. Chem. Res. (2009), 48, pp. 685-691.
Thacker et al. "Antidegadants", Handbook of Vinyl Formatting, 2008, pp. 77-78.
You et al.,"Chemical Recycling of Polyurethanes and Applications for the Recyclates", BASF Corporation, pp. 363-374.
International Search Report and Written Opinion mailed in PCT/US2015/057685 dated Jan. 29, 2016.
You et al., A New Era of Polyurethane Recycling—Fascia to Roof Rail: Sustainable Recycling in Automotive, Polyurethanes Expo (1999), pp. 377-382.
von Stein et al., "Salt-assisted Organic-acid-catalyzed depolymerization of cellulose", Green Chem. (2010) 12, 1844-1849.
Viana et al. "Chemical Recycling of PET by Catalyzed Glycolysis: Kinetics of the Heterogeneous Reaction", Chem. Eng. Journ. 173 (2011) 210-219.
Saucedo-Rivalcoba et al., "(Chicken feathers keratin)/polyerathane membranes", Appl. Phys. A (2011) 104:219-228.
Pierson et al., "Acid-Catalyzed Chitin Liquefaction in Ethylene Glycol", ACS Publications (2014) 2081-2089.
Shukla et al., "Zein, the Industrial Protein from Corn", Industrial Crops and Products 13 (2001) 171-192.
Kelsey et al. "High Impact, Amorphous Terephthalate Copolyesters of Rigid 2,2,4,4-Tetramethyl-1,3-cyclobutanediol with Flexible Diols", Macromolecules (2000), 33, 5810-5818.
Sun, "Enzymatic Hydrolysis of Soy Proteins and the Hydrolysates Utilisation", Int. Journ. of Food Science and Technology (2011), 46, 2447-2459.
Ullah et al., "Bioplastics from Father Quill", BioMacromolecules, ACS (2011), 3826-3832.
Frisch, "Progress in Recycling of Polyurethanes", Polimery (1998) 43, No. 10, 579-660.
Bouchard, et al. "Characterization of Depolymerized Cellulosic Residues", Wood Sci. Technol. (1990) 24: 159-169.
Lee et al., "Desaminated Glycolysis of Water-Blown Rigid Polyurethane Foams", Journal of Applied Polymer Science, vol. 77, (2000) 2646-2656.
"Fuel from Chicken Feathers?", www.alternative-energy-news.infofuel-from-chicken-feathers.pdf, Dec. 3, 2015.
Buggy et al. "Recovery of Polyol from Flexible Polyurethane Foam Wastes", Key Engineering Materials vols. 99-100 (1995) pp. 65-78.
Nagase et al., "Development of a Chemical Recycling Process for Waste Plastics Using Supercritical Water", Kobelco Technology Review No. 22, (Apr. 1999) 11-14.
Nikles et al., "New Motivation for the Depolymerization Products Derived from Poly(Ethylene Terephthalate) (PET) Waste: a Review", Macromol. Mater. Eng., (2005) 290, 13-30.

(56) References Cited

OTHER PUBLICATIONS

Sigma Product Information Sheet, "Zein from Maize", MWM/RXR, Oct. 2003.
Bartecka, et al., "Polyols Obtained from Chemical Recycling of Integral Polyurethanes Waste Used for the Production of Urethane-rubber Composites", Modern Polymeric Materials for Environmental Applications, vol. 3, (2008), pp. 5-8.
Zahedi et al. "Optimization of Phthalic/Maleic Anhydride-Endcapped PET Oligomers using Response Surface Method", Polymer Engineering and Science (2014), 419-429.
Mazurek et al. "PET Wastes utilization in the synthesis of aliphatic-aromatic polyurethane elastomers", Polym. Adv. Technol., (2014) 25, 1273-1284.
Kim et al., "Kinetics of Polycarbonate Glycolysis in Ethylene Glycol", Ind. Eng. Chem. Res. (2009), 48, 685-691.
Oku et al., "Chemical conversion of poly(carbonate) to bis(hydroxyethyl) ether of bisphenol A. An Approach to the chemical recycling of plastic wastes as monomers", Polymer 41 (2000) 6749-6753.
Wicks, Jr., et al., "Powder Coatings", Organic Coatings: Science and Technology, Third Ed., (2007) 548-571.
Tavano, "Protein hydrolysis using proteases: An important tool for food biotechnology", Journal of Molecular Catalysis B: Enzymatic 90 (2013) 1-11.
Datta, "Effect of glycols used as glycolysis agents on chemical structure and thermal stability of the produced glycolsyates", J. Therm. Anal. Calorim (2012) 109:517-520.
Chun et al. "Characterization and Improvement of the Recyclate Obtained from the Glycolysis Reaction of Waste MDI Based Polyurethane Foam", Polyurethane Con. 2000, Oct. 8-11, 2000 537-541.
Nikje et al. "Polyurethane Waste Reducation and Recycling: From Bench to Pilot Scales", Designed Monomers and Polymers 14:5 (2011) 395-421.
Sendijarevic et al., "Chemical Recycling of Mixed Polyurethane Foam Stream Recovered from Shredder Residue into Polyurethane Polyols", Journal of Cellular Plastics, vol. 43 (Jan. 2007) 30-46.
Molero et al., "Chemical recovery of flexible polyurethane foam wastes", WIT Transactions on Ecology and the Environment, vol. 140, (2010) pp. 69-81.
Molero et al., "Influence of the Use of Recycled Polyols Obtained by Glycolsysis on the Preparation and Physical Properties of Flexible Polyurethane", Journal of Applied Polymer Science, vol. 109 (2008) pp. 617-626.
Ulrich, "Recent Advances in Polyisocyanurate Technology", Int. Conf. (1980): Cellular and non-Cellular Polyurethanes; pp. 81-89.
Ritter, "BPA is Indispensible for Making Plastics" ACS—Chem. Eng. vol. 89, No. 23, (2011).
Leaversuch, "Thermoplastic Polyesters; It's a Good Time to Know Them Better", Plastics Technology, (Jun. 2004), pp. 46-51, 63-64.
European Commission Joint Research Centre "Survey of technologies for the recycling by chemolysis", (May 1996), IPTS, pp. 1-41.
Sun "Enzymatic hydrolysis of soy proteins and the hydrolysates utilisation", International Journal of Food Science and Technology (2011), 46, pp. 2447-2459.
Saint-Loup et al. "Synthesis of (polyethylene terephthalate/polye-caprolactone) copolyesters", Polymer 44, (2003) 3437-3449.
Mulder, "Proteins in Biomass Streams" Biorenewable Resources Platform, (Apr. 2010), 60 pages.
Schmid et al. "Thermoforming of whey protein-based barrier layers for application in food packaging", FS&T, vol. 25, Issue 3, (2011) pp. 34-35.
Floris et al., "Application of whey proteins as coating ingredients", NUTRAfoods (2010), 9(4) pp. 25-31.
Burkhart, "Silicone Surfactants, Unique Additives to Optimize Polyurethane Foam Manufacturing", 60 Years of Polyurethanes, International Symposium and Exhibition (1998) p. 375.
Boehme et al, "Synthesis and characterization of a novel unsaturated polyester based on poly(trimethylene)", Polymer (2006), 47(6), 1892-1898 CODEN: POLMAG; ISSN: 0032-3861.
Raudenbusch, "A novel concept for crosslinking surface coatings", Organic Coatings (1984), 7, 59-78 CODEN: ORGCD8; ISSN: 0883-2676 (abstract).
Ronda et al. "A renewable approach to thermosetting resins" Reactive & Functional Polymers (2013), 73(2), 381-395 CODEN: RFPOF6; ISSN: 1381-5148.
Zhang et al. "Study of liquefaction of wood and its components in polyhydric alcohol" Linehan Huaxue Yu Gongye (2012), 32(2), 14-20 CODEN: LHYGD7; ISSN: 0253-2417.
Lin, Recycling Technology of Poly(ethylene Terephthalate) Materials; Macromol. Symp. 135, (1998) 129-135.
International Search Report mailed in PCT/US2015/045972 dated Oct. 27, 2015, 3 pages.
International Search Report mailed in PCT/US2015/045978 dated Nov. 25, 2015, 5 pages.
Das et al. "Production of biofuel from chicken feathers" Int Journ. Power Eng and Energy (2013), 4:2; pp. 364-366.

\* cited by examiner

POLYESTER POLYOLS FROM RECYCLED POLYMERS AND WASTE STREAMS

RELATED APPLICATIONS

This application is a continuation U.S. Application under 35 U.S.C. § 365 of International Patent Application No. PCT/US2015/045792, filed on Aug. 19, 2015, which claims priority to U.S. Provisional Patent Application Ser. No. 62/039,816 filed on Aug. 20, 2014, U.S. Provisional Patent Application Ser. No. 62/039,820 filed on Aug. 20, 2014, U.S. Provisional Patent Application Ser. No. 62/082,974 filed on Nov. 21, 2014, U.S. Provisional Patent Application Ser. No. 62/110,343 filed on Jan. 30, 2015, U.S. Provisional Patent Application Ser. No. 62/110,347 filed on Jan. 30, 2015, and U.S. Provisional Patent Application Ser. No. 62/185,008 filed on Jun. 26, 2015, the disclosures of each of which are incorporated herein by reference in their entirety.

FIELD OF THE INVENTION

The present invention relates to polyester polyols made from an aromatic polyacid source, a glycol, and a digestible polymer. The polyols can be made by heating an aromatic polyacid source with a glycol to give a digested intermediate which is then reacted with a digestible polymer, which can be obtained from various recycled polymers and low value waste streams. The polyester polyols provide a sustainable alternative to petrochemical and biochemical based polyols, and are useful for making other polymers.

BACKGROUND OF THE INVENTION

Polyester polyols are commonly used intermediates for the manufacture of condensation polymers. These condensation polymers include polyurethane products such as flexible and rigid polymeric foams, polyisocyanurate foams, coatings, powder coatings, sealants, adhesives, and elastomers.

Commonly, the polyester polyol is made by condensing aromatic diacids, diesters, or anhydrides (e.g., terephthalic acid, dimethyl terephthalate) with glycols such as ethylene glycol, propylene glycol, diethylene glycol, or the like. These starting materials usually derive exclusively from petrochemical sources.

As companies increasingly seek to offer products with improved sustainability, the availability of intermediates produced from bio-renewable and/or recycled materials becomes more leveraging. However, there remains a need for these products to deliver equal or better performance than their traditional petroleum-based alternatives at a comparable price point.

Bio-renewable content alone can be misleading as an indicator of "green" chemistry. For example, when a food source such as corn is needed to provide the bio-renewable content, there are clear trade-offs between feeding people and providing them with performance-based chemical products. Additionally, the chemical or biochemical transformations needed to convert sugars or other bio-friendly feeds to useful chemical intermediates such as polyols can consume more natural resources and energy, and can release more greenhouse gases and pollutants into the environment than their petro-based alternatives in the effort to achieve "green" status.

Waste thermoplastic polyesters, including waste polyethylene terephthalate (PET) streams (e.g., from plastic beverage containers), provide an abundant source of raw material for making new polymers. Usually, when PET is recycled, it is used to make new PET beverage bottles, PET fiber, or it is chemically transformed to produce polybutylene terephthalate (PBT). Other recycled raw materials are also available. For example, recycled propylene glycol is available from aircraft or RV deicing and other operations, and recycled ethylene glycol is available from spent vehicle coolants.

Urethane formulators demand polyols that meet required specifications for color, clarity, hydroxyl number, functionality, acid number, viscosity, and other properties. These specifications will vary and depend on the type of urethane application. For instance, rigid foams generally require polyols with higher hydroxyl numbers than the polyols used to make flexible foams.

Polyols suitable for use in making high-quality polyurethanes have proven difficult to manufacture from recycled materials, including recycled polyethylene terephthalate (rPET). Many references describe digestion of rPET with glycols (also called "glycolysis"), usually in the presence of a catalyst such as zinc or titanium. Digestion converts the polymer to a mixture of glycols and low-molecular-weight PET oligomers. Although such mixtures have desirably low viscosities, they often have high hydroxyl numbers or high levels of free glycols. Frequently, the target product is a purified bis(hydroxyalkyl) terephthalate (see, e.g., U.S. Pat. Nos. 6,630,601, 6,642,350, and 7,192,988) or terephthalic acid (see, e.g., U.S. Pat. No. 5,502,247). Some of the efforts to use glycolysis product mixtures for urethane manufacture are described in a review article by D. Paszun and T. Spychaj (*Ind. Eng. Chem. Res.* 36 (1997) 1373.

Most frequently, ethylene glycol is used as the glycol reactant for glycolysis. This is sensible because it minimizes the possible reaction products. Usually, the glycolysis is performed under conditions effective to generate bis(hydroxyethyl) terephthalate ("BHET"), although sometimes the goal is to recover pure terephthalic acid. When ethylene glycol is used as a reactant, the glycolysis product is typically a crystalline or waxy solid at room temperature. Such materials are less than ideal for use as polyol intermediates because they must be processed at elevated temperatures. Polyols are desirably free-flowing liquids at or close to room temperature.

The safe disposal or reuse of waste materials from various sources is an environmental and economic challenge. Such wastes had typically gone into landfills, but as landfill capacity is becoming ever scarcer and disposal costs are continuously increasing, cost effective and environmentally acceptable alternatives are needed to deal with these waste materials. Waste streams are produced by a great range of industries and sources, including, e.g., the plastics industry, the automobile industry, the paper industry, consumers, the agricultural industry, including both crop and animal production, as well as the production of animal products (e.g., the dairy, egg, and wool industries). Because of these environmental and cost challenges, there is a need to find practical uses for recycled polymers and waste streams. In other words, there is the need to utilize recycled polymers and waste streams to produce new polymers and building blocks for these new polymers.

Chemolysis, which is the chemical breakdown or decomposition of an organic molecule into smaller molecules, may provide a route for recycling of polymeric materials. Chemolysis is essentially a depolymerization process and can be viewed as the opposite of a polycondensation process to make a polymer. Chemolysis is usually applied to condensation polymers such as PET, polyurethanes, or polyamides.

However, chemolysis is not applicable to polymers such as vinyls, acrylics, fluoroplastics and polyolefins, and by some estimates not applicable to more than about 10% of plastics waste. See, e.g., "Survey of current projects for plastics recycling by chemolysis", European Commission Joint Research Centre, Institute for Prospective Technological Studies, Seville, May 1996. Therefore, the recycling or chemolysis of many recycle polymers and waste streams presents significant technical challenges.

In many instances, it would be highly desirable to have improved polyester polyols. In particular, the urethane industry needs sustainable polyester polyols based in substantial part on recycled polymers or waste streams. This scenario would provide a viable means for consuming these recycle waste streams. Furthermore, polyester polyols with high recycle content that satisfy the demanding viscosity, functionality, hydroxyl content, and performance requirements of formulators, such as polyurethane formulators, would be valuable.

It is apparent from the above there is an ongoing need for sustainable sources of polyester polyols which at the same time can help to both reduce waste streams, and provide further options for using under-utilized recycled polymer streams.

SUMMARY OF THE INVENTION

The present invention relates to polyester polyols made from polyacid sources such as thermoplastic polyesters. The polyols can be made, for example, by heating a thermoplastic polyester such as virgin PET, recycled PET, or mixtures thereof, with a glycol to give a digested intermediate which is then reacted with a digestible or glycolyzable polymer, e.g., a digestible or glycolyzable condensation or addition polymer. The digestible polymer can be obtained from various recycle polymers and waste streams. The polyester polyols can comprise a glycol-digested aromatic polyacid source, such as a glycol-digested thermoplastic polyester and the material obtained from digestible polymer. The resulting polyester polyols provide a sustainable alternative to petrochemical or biochemical based polyester polyols.

We surprisingly found that high-recycle-content polyols having desirable hydroxyl numbers, viscosities, appearance, and other attributes useful for formulating polyurethane products can be made by reacting, at certain equivalent ratios, a glycol-digested thermoplastic polyester, preferably a digested PET, and a digestible polymer, as defined herein. The polyols, which are valuable for formulating a variety of polyurethanes and related products—including polyurethane dispersions, flexible and rigid polymeric foams, coatings, powder coatings, adhesives, sealants, and elastomers—provide a sustainable alternative to bio- or petrochemical-based polyols.

DETAILED DESCRIPTION OF THE INVENTION

The present invention relates to a polyester polyol made by a process comprising: (a) heating an aromatic polyacid source with a glycol to give a digested intermediate; and (b) reacting the resulting digested intermediate with a digestible polymer containing a functional group selected from an ester, amide, ether, carbonate, urea, carbamate, glycoside, and isocyanurate, or combinations thereof; wherein the molar ratio of glycol to aromatic polyacid source is at least 0.8, and the polyester polyol has a hydroxyl number within the range of about 10 to about 800 mg KOH/g.

In one aspect the present invention relates to a polyester polyol wherein the aromatic polyacid source is a thermoplastic polyester.

In another aspect the present invention relates to a polyester polyol wherein the thermoplastic polyester is selected from copolymers of: (a) acids selected from terephathlic acid, 2,5-furandicarboxylic acid, isophthalic acid, dihydroferulic acid, salts thereof, C1-C6 monoesters thereof, C1-C6 diesters thereof, and combinations thereof; and (b) diols selected from ethylene glycol, 1,2-propanediol, 1,3-propanediol, 1,2-butanediol, 1,3-butanediol, 1,4-butanediol, 2,3-butanediol, 1,3-cyclohexane diol, 1,4-cyclohexane diol, 1,3-cycohexanedimethanol, 1,4-cyclohexanedimethanol, 2,2,4,4-tetramethyl-1,3-cyclobutane diol, and combinations thereof.

In another aspect the present invention relates to a polyester polyol wherein the thermoplastic polyester is selected from polyethylene terephthalate (PET), polybutylene terephthalate, polytrimethylene terephthalate (PTT), glycol-modified polyethylene terephthalate, copolymers of terephthalic acid and 1,4-cyclohexanedimethanol, isophthalic acid-modified copolymers of terephthalic acid and 1,4-cyclohexanedimethanol, copolymers of 2,5-furandicarboxylic acid or C1-C6-dialkyl 2,5-furandicarboxylates, copolymers of terephthalic acid and 2,2,4,4-tetramethyl-1, 3-cyclobutane diol, and combinations thereof.

In another aspect the present invention relates to a polyester polyol wherein the thermoplastic polyester is selected from virgin PET and recycled PET, or combinations thereof.

In another aspect the present invention relates to a polyester polyol wherein the recycled PET is obtained from recycled bottles.

In another aspect the present invention relates to a polyester polyol wherein the recycled PET is obtained from recycled textiles.

In another aspect the present invention relates to a polyester polyol wherein the recycled PET is obtained from recycled carpeting.

In another aspect the present invention relates to a polyester polyol wherein the thermoplastic polyester is selected from virgin PTT and recycled PTT, or combinations thereof.

In another aspect the present invention relates to a polyester polyol wherein the recycled PTT is obtained from recycled textiles.

In another aspect the present invention relates to a polyester polyol wherein the recycled PTT is obtained from recycled carpeting.

In another aspect the present invention relates to a polyester polyol wherein the thermoplastic polyester is a copolymer of terephthalic acid and 2,2,4,4-tetramethyl-1,3-cyclobutane diol.

In another aspect the present invention relates to a polyol wherein the glycol is selected from ethylene glycol, propylene glycol, 1,3-propanediol, 1,2-butylene glycol, 1,3-butylene glycol, 1,4-butanediol, 2-methyl-1,3-propanediol, neopentyl glycol, glycerol, trimethylolpropane, 3-methyl-1,5-pentanediol, 1,4-cyclohexanedimethanol, diethylene glycol, tetraethylene glycol, dipropylene glycol, triethylene glycol, tripropylene glycol, polyethylene glycol, polypropylene glycol, erythritol, pentaerythritol, sorbitol, and block or random copolymer glycols s of ethylene oxide and propylene oxide, or combinations thereof.

In another aspect the present invention relates to a polyester polyol wherein the glycol comprises a recycled glycol.

In another aspect the present invention relates to a polyester polyol having a hydroxyl number within the range of about 10 to about 800 mg KOH/g.

In another aspect the present invention relates to a polyester polyol having a hydroxyl number within the range of about 25 to about 500 mg KOH/g.

In another aspect the present invention relates to a polyester polyol having a hydroxyl number within the range of about 35 to about 400 mg KOH/g.

In another aspect the present invention relates to a polyester polyol having a hydroxyl number within the range of about 50 to about 400 mg KOH/g.

In another aspect the present invention relates to a polyester polyol wherein the weight percent of digestible polymer incorporated into the polyester polyol is from about 1% to about 75%.

In another aspect the present invention relates to a polyester polyol wherein the weight percent of digestible polymer incorporated into the polyester polyol is from about 3% to about 60%.

In another aspect the present invention relates to a polyester polyol wherein the weight percent of digestible polymer incorporated into the polyester polyol is from about 5% to about 45%.

In another aspect the present invention relates to a polyester polyol having a viscosity at 125° C. less than about 5000 cP.

In another aspect the present invention relates to a polyester polyol having a viscosity at 25° C. less than about 20,000 cP.

In another aspect the present invention relates to a polyester polyol having a viscosity at 25° C. less than about 10,000 cP.

In another aspect the present invention relates to a transparent polyester polyol.

In another aspect the present invention relates to a polyester polyol having a recycle content as defined herein greater than 50 wt %.

In another aspect the present invention relates to a polyester polyol wherein the aromatic polyacid source and glycol are heated in the presence of a titanium catalyst.

In another aspect the present invention relates to a polyester polyol wherein the aromatic polyacid source and glycol are heated at a temperature within the range of about 80° C. to about 260° C.

In another aspect the present invention relates to a polyester polyol having an acid number of less than 10 mg KOH/g.

In another aspect the present invention relates to a polyester polyol wherein the digestible polymer is selected from digestible condensation polymers and digestible addition polymers, or combinations thereof.

In another aspect the present invention relates to a polyester polyol wherein the digestible polymer is a digestible condensation polymer.

In another aspect the present invention relates to a polyester polyol wherein the digestible polymer is a digestible addition polymer.

In another aspect the present invention relates to a polyester polyol wherein the digestible polymer is selected from polylactic acids, synthetic (i.e. man-made) polyamides, polycarbonates, polyurethanes, polyisocyanurates, polyethers, proteins, polysaccharides, polylactones, and polylactams, or combinations thereof.

In another aspect the present invention relates to a polyester polyol wherein the digestible polymer is selected from polylactic acids.

In another aspect the present invention relates to a polyester polyol wherein the digestible polymer is selected from synthetic polyamides.

In another aspect the present invention relates to a polyester polyol wherein the digestible polymer is selected from polycarbonates.

In another aspect the present invention relates to a polyester polyol wherein the digestible polymer is selected from polyurethanes.

In another aspect the present invention relates to a polyester polyol wherein the digestible polymer is selected from polyisocyanurates.

In another aspect the present invention relates to a polyester polyol wherein the digestible polymer is selected from polyethers.

In another aspect the present invention relates to a polyester polyol wherein the digestible polymer is selected from proteins.

In another aspect the present invention relates to a polyester polyol wherein the digestible polymer is selected from polysaccharides.

In another aspect the present invention relates to a polyester polyol wherein the digestible polymer is selected from polylactones.

In another aspect the present invention relates to a polyester polyol wherein the digestible polymer is selected from polylactams.

In another aspect the present invention relates to a polyester polyol wherein the synthetic (man-made) polyamide is selected from nylon-6, nylon-6,6, nylon-6,9, nylon-6,10, nylon-6,12, nylon-11, nylon-12, nylon-4,6, and aramids, such as for example para-aramids, or combinations thereof.

In another aspect the present invention relates to a polyester polyol wherein the synthetic polyamide is selected from virgin nylon-6, recycled nylon-6, virgin nylon-6,6, and recycled nylon-6,6, or combinations thereof.

In another aspect the present invention relates to a polyester polyol wherein the recycled nylon-6 or the recycled nylon-6,6 is obtained from recycled.

In another aspect the present invention relates to a polyester polyol wherein the polycarbonate is poly(bisphenol A carbonate), also known as PBAC.

In another aspect the present invention relates to a polyester polyol wherein the polycarbonate is recycled poly(bisphenol A carbonate), also known as rPBAC.

In another aspect the present invention relates to a polyester polyol wherein the protein is selected from keratin, collagen, casein, whey, zein, silk, wool or combinations thereof.

In another aspect the present invention relates to a polyester polyol wherein the protein is keratin.

In another aspect the present invention relates to a polyester polyol wherein the protein is collagen.

In another aspect the present invention relates to a polyester polyol wherein the protein is casein.

In another aspect the present invention relates to a polyester polyol wherein the protein is whey.

In another aspect the present invention relates to a polyester polyol wherein the protein is zein.

In another aspect the present invention relates to a polyester polyol wherein the protein is soy protein.

In another aspect the present invention relates to a polyester polyol wherein the protein is silk.

In another aspect the present invention relates to a polyester polyol wherein the protein is wool.

In another aspect the present invention relates to a polyester polyol wherein the keratin is selected from avian feathers.

In another aspect the present invention relates to a polyester polyol wherein the avian feathers are selected from vaned feathers and down feathers, or combinations thereof.

In another aspect the present invention relates to a polyester polyol wherein the avian feathers are selected from chicken feathers, chicken down feathers, turkey feathers, turkey down feathers, duck feathers, duck down feathers, goose feathers, goose down feathers, or combinations thereof.

In another aspect the present invention relates to a polyester polyol wherein the avian feathers are chicken feathers.

In another aspect the present invention relates to a polyester polyol wherein the avian feathers are chicken down feathers.

In another aspect the present invention relates to a polyester polyol wherein the avian feathers are turkey feathers.

In another aspect the present invention relates to a polyester polyol wherein the avian feathers are turkey down feathers.

In another aspect the present invention relates to a polyester polyol wherein the avian feathers are duck feathers.

In another aspect the present invention relates to a polyester polyol wherein the avian feathers are duck down feathers.

In another aspect the present invention relates to a polyester polyol wherein the avian feathers are goose feathers.

In another aspect the present invention relates to a polyester polyol wherein the avian feathers are down feathers.

In another aspect the present invention relates to a polyester polyol wherein the keratin is obtained from feather meal.

In another aspect the present invention relates to a polyester polyol wherein the polysaccharide is selected from pectin, polyglucosides, and sulphated polysaccharides, or combinations thereof.

In another aspect the present invention relates to a polyester polyol wherein the polysaccharide is pectin.

In another aspect the present invention relates to a polyester polyol wherein the polysaccharide is a polyglucoside.

In another aspect the present invention relates to a polyester polyol wherein the polysaccharide is a sulphated polysaccharide.

In another aspect the present invention relates to a polyester polyol wherein the polyglucoside is selected from starch, rayon, cellulose, hemicellulose, cellophane, and chitin, or combinations thereof.

In another aspect the present invention relates to a polyester polyol wherein the polyglucoside is starch.

In another aspect the present invention relates to a polyester polyol wherein the starch is selected from helical amylose, amylopectin, and glycogen, or combinations thereof.

In another aspect the present invention relates to a polyester polyol wherein the starch is helical amylose.

In another aspect the present invention relates to a polyester polyol wherein the starch is amylopectin.

In another aspect the present invention relates to a polyester polyol wherein the starch is glycogen.

In another aspect the present invention relates to a polyester polyol wherein the polyglucoside is rayon.

In another aspect the present invention relates to a polyester polyol wherein the polyglucoside is cellulose.

In another aspect the present invention relates to a polyester polyol wherein the polyglucoside is hemicellulose.

In another aspect the present invention relates to a polyester polyol wherein the polyglucoside is cellophane.

In another aspect the present invention relates to a polyester polyol wherein the polyglucoside is chitin.

In another aspect the present invention relates to a polyester polyol wherein the sulphated polysaccharide is carrageenan.

In another aspect the present invention relates to a polyester polyol made by a process comprising reacting an aromatic polyacid source, a glycol, and a digestible polymer containing a functional group selected from an ester, amide, ether, carbonate, urea, carbamate, glycoside, and isocyanurate group, or combinations thereof; wherein the molar ratio of glycol to aromatic polyacid source is at least 1.0, and the polyester polyol has a hydroxyl number within the range of about 10 to about 800 mg KOH/g.

In another aspect the present invention relates to a polyester polyol comprising recurring units of: (a) a glycol-digested aromatic polyacid source, and (b) an intermediate made by digesting a digestible polymer containing a functional group selected from an ester, amide, ether, carbonate, urea, carbamate, glycoside, and isocyanurate group, or combinations thereof.

In another aspect the present invention relates to a polyester polyol comprising recurring units generated from: (a) an aromatic polyacid source, and (b) a digestible polymer containing a functional group selected from an ester, amide, ether, carbonate, urea, carbamate, glycoside, and isocyanurate group, or combinations thereof.

In another aspect the present invention relates to a polyester polyol further comprising recurring units of a glycol.

In another aspect the present invention relates to a polyester polyol wherein the polyacid source is other than orthophthalic acid or phthalic anhydride.

In another aspect the present invention relates to a polyester polyol wherein (a) when the polyacid source is selected from terephthalic acid, isophthalic acid, and orthophthalic acid, or esters or anhydrides thereof, or combinations of said acids, esters, or anhydrides thereof, (b) the digestible polymer contains a functional group selected from an ester, amide, ether, carbonate, urea, and glycoside group, or combinations thereof.

In another aspect the present invention relates to a polyester polyol wherein (a) when the polyacid source is selected from terephthalic acid, isophthalic acid, or esters thereof, or combinations of said acids or esters thereof, (b) the digestible polymer contains a functional group selected from an ester, amide, ether, carbonate, urea, carbamate, glycoside, and isocyanurate group, or combinations thereof.

In another aspect the present invention relates to a polyester polyol further comprising a hydrophobe or nonionic surfactant, or combinations thereof In another aspect the present invention relates to a polyester polyol wherein the hydrophobe or nonionic surfactant is selected from ricinoleic acid, castor oil, ethoxylated castor oil, saturated or unsaturated $C_9$-$C_{18}$ dicarboxylic acids, vegetable oils, fatty acids, fatty acid esters, modified vegetable oils, fatty triglycerides, cardanol-based products, recycled cooking oil, isostearyl alcohol, hydroxy-functional materials derived from epoxidized, ozonized, or hydroformylated fatty esters, dimer fatty acids, block copolymers of ethylene oxide with propylene oxide, alkoxylated alkyl phenols, alkoxylated fatty alcohols, or combinations thereof.

In another aspect the present invention relates to a polyester polyol wherein the glycol-digested aromatic polyacid source is a glycol-digested thermoplastic polyester.

In another aspect the present invention relates to a polyurethane made from a polyester polyol of the present invention.

In another aspect the present invention relates to a polyurethane comprising a polyester polyol of the present invention.

In another aspect the present invention relates to a polyurethane, prior to mixing with any other components, comprising a polyester polyol of the present invention In another aspect the present invention relates to an aqueous polyurethane dispersion made from a polyester polyol of the present invention.

In another aspect the present invention relates to an aqueous polyurethane dispersion comprising a polyester polyol of the present invention.

In another aspect the present invention relates to a coating made from a polyester polyol of the present invention.

In another aspect the present invention relates to a coating comprising a polyester polyol of the present invention.

In another aspect the present invention relates to a coating, prior to mixing with any other components, comprising a polyester polyol of the present invention.

In another aspect the present invention relates to a coating selected from liquid coatings and powder coatings.

In another aspect the present invention relates to a liquid coating comprising a polyester polyol of the present invention.

In another aspect the present invention relates to a liquid coating comprising from 1% to 95% by weight of the polyester polyol of the present invention.

In another aspect the present invention relates to a liquid coating that is a polyurethane coating.

In another aspect the present invention relates to a powder coating comprising a polyester polyol of the present invention.

In another aspect the present invention relates to a powder coating, prior to mixing with any other components, comprising a polyester polyol of the present invention.

In another aspect the present invention relates to a powder coating comprising from 1% to 95% by weight of the polyester polyol of the present invention.

In another aspect the present invention relates to a powder coating having at least one glass transition temperature, $T_g$, greater than or equal to 45° C.

In another aspect the present invention relates to a powder coating having at least one melting point greater than or equal to 45° C.

In another aspect the present invention relates to a powder coating further comprising a material selected from a crosslinking agent, a flow control agent, a degassing agent, a catalyst, and combinations thereof.

In another aspect the present invention relates to a powder coating further comprising a pigmenting material.

In another aspect the present invention relates to a metal substrate coated with a coating material of the present invention.

In another aspect the present invention relates to a coated metal substrate composition comprising a metal substrate and a coating material of the present invention.

In another aspect the present invention relates to a polymeric foam made from a polyester polyol of the present invention.

In another aspect the present invention relates to a polymeric foam comprising a polyester polyol of the present invention.

In another aspect the present invention relates to a polymeric foam, prior to mixing with any other components, comprising a polyester polyol of the present invention.

In another aspect the present invention relates to a polymeric foam that is a rigid polyurethane foam.

In another aspect the present invention relates to a polymeric foam that is a polyisocyanurate foam.

In another aspect the present invention relates to an acrylate or polyacrylate made from the polyester polyols of the present invention.

In another aspect the present invention relates to an acrylate or polyacrylate comprising a polyester polyol of the present invention.

In another aspect the present invention relates to a process for making a polyester polyol comprising: (a) heating an aromatic polyacid source with a glycol to give a digested intermediate;

and (b) reacting the resulting digested intermediate with a digestible polymer containing a functional group selected from an ester, amide, ether, carbonate, urea, carbamate, glycoside, and isocyanurate group, or combinations thereof; wherein the molar ratio of glycol to aromatic polyacid source is at least 0.8, and the polyester polyol has a hydroxyl number within the range of about 10 to about 800 mg KOH/g.

In another aspect the present invention relates to a process for making a polyester polyol comprising reacting an aromatic polyacid source, a glycol, and a digestible polymer containing a functional group selected from an ester, amide, ether, carbonate, urea, carbamate, glycoside, and isocyanurate group, or combinations thereof; wherein the molar ratio of glycol to aromatic polyacid group is at least 0.8, and the polyester polyol has a hydroxyl number within the range of about 10 to about 800 mg KOH/g.

Definitions

As used herein, the following terms have the indicated meanings unless expressly stated to the contrary:

The term "digestible polymer" as used herein and described in more detail below refers to a polymer component of the processes and compositions of the present invention that is capable of being broken down or degraded into smaller polymeric, oligomeric, or monomeric components via a chemical reaction, with the digested aromatic polyacid source, e.g., a thermoplastic polyester, of the processes and compositions herein. The digestible polymer is distinct from and should not be confused with the aromatic polyacid source, e.g., a thermoplastic polyester, which is also digested. An example of a chemical reaction in which the digestible polymer is digested or broken down is glycolysis. A variety of digestible polymers useful herein are described below. The source of these polymers can be recycled polymers and waste streams.

The term "functional group" as used herein refers to specific groups of atoms or bonds within molecules that are responsible for the characteristic chemical reactions or properties of those molecules. The same functional group will generally undergo the same or similar chemical reaction(s) regardless of the size of the molecule it is a part of. However, the relative reactivity of a functional group can be modified by nearby functional groups and the degree of crosslinking found in the digestible polymer. The word moiety or the term chemical moiety is often used synonymously with "functional group" but, according to the IUPAC definition, a moiety is a part of a molecule that may include either whole functional groups or parts of functional groups as substructures. For example, an ester, —RCOOR'—, has an ester functional group, —C(=O)OR—, and is composed of an alkoxy moiety, —OR', and an acyl moiety, RC(=O)—, or, equivalently, an ester functional group may be divided into carboxylate, RC(=O)O—, and alkyl, —R', moieties. Note that R and R' represent the remainder of the molecule to which the functional group or moiety is attached, in this example R and R' being carbon-containing groups such as alkyl groups. Nonlimiting examples of functional groups include those found in the digestible polymers of the present invention:

Ester, or —C(═O)O— (in this instance the O— is attached to the carbon of a carbon containing chemical group);

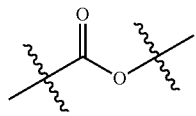 [SMILES: *OC(*)=O]

Amide, or —C(═O)NR—, in this instance R is H or a carbon-containing group;

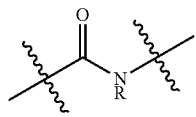

Ether, —ROR'—, in this instance R and R' are independently the same or different carbon-containing groups;

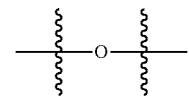 [SMILES: *O*]

Carbonate, —OC(═O)O—;

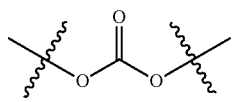 [SMILES: *OC(=O)O*]

Urea, also known as carbamide, —NRC(═O)NR'—, in this instance R and R' are independently H or a carbon-containing group;

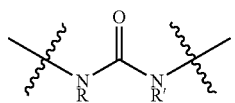

Carbamate, also known as urethane, —OC(═O)NR—, in this instance R is H or a carbon-containing group;

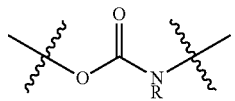

Glycoside, i.e. a molecule in which a sugar is bound to another sugar or functional group via a glycosidic linkage. The following chemical structure of the compound sucrose, is a nonlimiting example, illustrating the glycosidic linkage of the sugars glucose and fructose in the dissacharide sucrose.

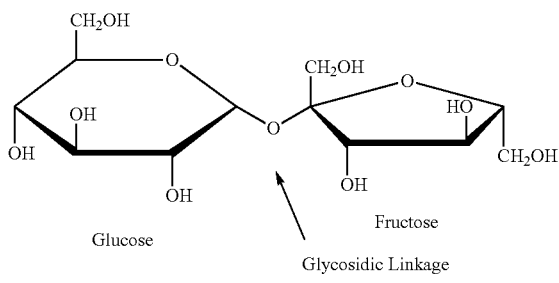

Sucrose Molecule Illustraing Glycosidic Linkage

Isocyanurate, i.e. a 6-membered ring system containing alternating substituted nitrogen and carbonyl groups, that is usually derived from a diisocyanate. In this instance R and R' are independently selected from a carbon-containing group.

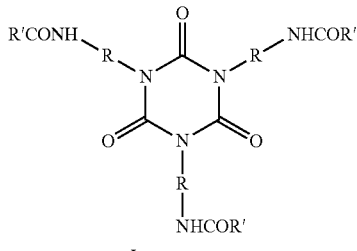

Isocyanuarate

The term "glycolysis" as used herein is from the field of polymer chemistry where it refers to the digestion of a polymer with a glycol via a chemical reaction to yield lower molecular weight fragments, such as for example, oligomers and monomers.

The terms "waste stream" as used herein refers to waste or discarded products from industry, agriculture, or consumer sources that has few ultimate destinations or applications other than for example, landfill, incineration, animal feed, concrete, burning as a source of energy, fertilization, landscaping mulch, or other relatively low value applications.

The term "recycled polymer" as used herein refers to a polymer that has little value after its original lifespan has ended, and is recovered in an economically viable fashion from the original spent application for use in other applications.

Digestible Polymers

The compositions and processes of the present invention comprise a digestible polymer. These digestible polymers have or contain a functional group selected from ester, amide, ether, carbonate, urea (i.e. carbamide), carbamate (i.e. urethane), glycoside, and isocyanurate groups, or combinations thereof. The digestible polymers are such that they are capable of being "digested" or broken down or degraded into smaller polymeric, oligomeric, or monomeric components via a chemical reaction, which can include an enzymatic reaction.

The digestible polymers can be selected from condensation polymers, addition polymers, or combinations thereof. Condensation polymers are formed via a condensation reaction where the monomers are joined together and lose a small molecule, such as water, ammonia, or a low molecular weight alcohol, e.g., methanol or ethanol, as a byproduct. Addition polymers are formed via the chemical addition of monomers without the loss of a small molecule byproduct. For the purposes of this invention, addition polymers are generally made by the ring opening and addition of monomers such as lactones, lactams and epoxides to an initiator molecule such as an amine or alcohol, by the addition of monomers such as di- or poly-isocyanates to active hydrogen containing polyols or amines to form polyurethanes, or by the trimerization of di- or poly-isocyanates to form isocyanurates.

The digestible polymers of the present invention are selected from polylactic acids (PLAs), synthetic polyamides, polycarbonates, polyurethanes, polyisocyanurates (PR), polyethers, proteins, polysaccharides, or combinations thereof. Of the foregoing, the polylactic acids (PLAs), synthetic polyamides, polycarbonates, proteins, and polysaccharides are generally considered condensation polymers. However, polylactones, which are made from lactone monomers such as, for example caprolactone, and polylactams, which are essentially polyamides that have been made from lactam monomers such as, for example caprolactam, are generally considered addition polymers. Polyethers may be prepared via the condensation of alcohols, however, they are usually prepared by the addition reaction of monomers such as ethylene oxide, propylene oxide and tetrahydrofuran to active hydrogen-containing initiators such as alcohols, glycols or amines. Additionally, polylactic acid may be prepared via the either the addition reaction of lactide to active hydrogen containing inititators or the condensation reaction of lactic acid with itself. Finally, polyurethanes and polyisocyanurates (PIR) are usually prepared via the addition polymerization of a di- or poly-isocyanurate with an active hydrogen substance such as a polyol or amine, or via the dimerization or trimerization of di- or poly-isocyanates to form uretidine diones and isocyanurates, respectively. It should also be noted that the characterization of the polymers according to the foregoing categories is conventional and for convenience. However, it is recognized that there is some overlap amongst the categories. For example, polyamides, polylactams, and proteins all contain amide functional groups, even though for convenience, they are being described separately. Similarly, polylactic acids and polylactones both contain ester functional groups.

Furthermore, the digestible polymers can contain more than one type of functional group. Examples of such polymers containing multiple functional groups are polyurethanes and polyisocyanurates, which may contain ether, ester, urethane and isocyanurate groups. Other digestible polymers are block copolymers having repeating blocks or segments of different polymerized monomers. Also, alloys, blends, composites or combinations of more than one kind of digestible polymer are within the scope of the present invention.

It should be noted that the digestible polymers as described herein in this section are considered separate from and are a distinct component of the present invention, from the materials described in the "Aromatic Polyacid Source" section, below.

The digestible polymers can be obtained from recycled polymers and waste streams. In fact, in view of green chemistry and sustainability considerations, it is highly desirable to use digestible polymers from such sources. The digestible polymer may further be obtained from virgin or newly manufactured sources. This latter choice makes sense in cases where the additional performance benefit obtained by digesting the newly manufactured polymer provides a value-added benefit to the resulting polyester polyol product.

Digestion Medium for the Digestible Polymer

The digestible polymers can be digested with a material from the digestion of an aromatic polyacid source. Various polyacid sources are useful for being digested to provide the digestion medium, including a thermoplastic polyester. Examples of such thermoplastic polyesters include polyethylene terephthalate (PET), polybutylene terephthalate, polytrimethylene terephthalate, glycol-modified polyethylene terephthalate, copolymers of terephthalic acid and 1,4-cyclohexanedimethanol, isophthalic acid-modified copolymers of terephthalic acid and 1,4-cyclohexanedimethanol, copolymers of 2,5-furandicarboxylic acid or dialkyl 2,5-furandicarboxylates, or combinations thereof. One or more glycols can also be used with the material described above in this paragraph. These glycols can be the same as those described below in the "Glycols" section. Examples of preferred glycols include ethylene glycol, propylene glycol, diethylene glycol, and polyethylene glycols with molecular weights less than about 400, and combinations thereof.

Also, as described herein, the polyester polyols can be made in a one pot or one reactor system in which the polyacid source, the glycol, and the digestible polymer are combined such that the polyacid source and the glycol form the digestion material in the presence of the digestible polymer and thus digest the digestible polymer.

The following are examples of digestible polymers useful herein.

Polylactic Acids (PLAs)

Polylactic acids (PLAs) are digestible polymers useful herein. Polylactic acids are thermoplastic aliphatic polyesters. They are biodegradable and are usually derived from renewable resources, such as corn starch; tapioca roots, chips or starch, or sugarcane. In 2010, PLA had the second highest consumption volume of any bioplastic in the world. See, Market Study Bioplastics, Ceresana, December 2011. An example of a polylactic acid useful herein includes Ingeo polylactic acid, supplied by Natureworks LLC. Although the recycle of PLA is in its infancy, examples exist such as closed loop recycling in sports stadiums, where cups, utensils and other food and beverage packaging within the stadium are entirely based on PLA, permitting ease of recycle.

Synthetic Polyamides

Synthetic, i.e. man-made polyamides are digestible polymers useful herein. These polymers have repeating units linked by amide functional groups. The term "synthetic" or "man-made", as used herein is to distinguish these digestible polymers from the proteins, which contain "amide" or "peptide" linkages, described below. Synthetic polyamides can be made through step-growth polymerization or solid-phase synthesis, examples being nylons, aramids, and sodium poly(aspartate). Synthetic polyamides are commonly used in textiles, automotives, carpet and sportswear due to their extreme durability and strength. Examples of man-made polyamides useful herein include the nylons such as nylon-6, nylon-6,6, nylon-6,9, nylon-6,10, nylon-6,12, nylon-11, nylon-12, nylon-4,6, and the aramids and para-aramids such as Kevlar, Technora, Twaron, Heracron, and Nomex. An example of a biobased polyamide includes PA 11, which is a biopolymer derived from natural oil. It is supplied by Arkema under the tradename Rilsan B. A similar biobased polyamide is Polyamide 410 (PA 410), derived from castor oil produced by DSM under the trade name EcoPaXX. Sources of recycled polyamides include nylon scrap from industry including injection molded automotive parts and post-consumer or post industrial scrap or waste such as textiles, fabrics and nylon carpet.

Polycarbonates

Polycarbonates are digestible polymers useful herein. Polycarbonates are polymers containing repeating units connected by carbonate functional groups. Many polycarbonates of commercial interest are derived from rigid monomers. A balance of useful features including temperature resistance, impact resistance and optical properties position polycarbonates between commodity plastics and engineering plastics. Polycarbonates can be produced by the reaction of bisphenol A (BPA) and phosgene. The resulting polymer is known as poly(bisphenol A carbonate), i.e. PBAC. It is found that recycled poly(bisphenol A carbonate), i.e. rPBAC, can also be used in the digestion. Furthermore, we have found that poly(bisphenol A carbonate) can be transreacted with rPET content polyols to form poly(ester/carbonate) hybrid polyols. Although the chemolysis of polycarbonates is known, none of the scientific works studied the use of aromatic polyester polyols as glycolyzing agents for rPBAC. See A. Oku, S. Tanaka, S. Hata, *Polymer* 41 (2000) 6749-6753; D. Kim, B., Kim, Y. Cho, M. Han, B., Kim, *Ind. Eng. Chem. Res.* (2009), 48, 685-691; and C. Lin, H. Lin, W. Liao, S. A. Dai, *Green Chemistry*, (2007), 9, 38-43.

Examples of polycarbonates useful here include Lexan®, Calib®, and Makrolon®. Polycarbonate is coded 7 implying that it is difficult to recycle, however, polycarbonate bottles and CDs are being extensively recycled. One method of recycling polycarbonate is by chemical recycling. PC is made to react with phenol in the presence of a catalyst to form BPA and DPC monomers. After purification, both these monomers are used to produce the polymer. The current invention provides an improved method for recycling polycarbonate thermoplastics.

Polyurethanes

Polyurethanes (PUs or PURs) are digestible polymers useful herein. Polyurethanes are polymers composed of a chain of organic units joined by carbamate (urethane) linkages. Most polyurethanes are thermosetting polymers that do not melt when heated, however, thermoplastic polyurethanes are also available. Polyurethanes are typically formed by reacting a di- or polyisocyanate with a polyol. Both the isocyanates and polyols used to make polyurethanes contain on average two or more functional groups per molecule. Polyurethanes are used in the manufacture of many commercially important items, including flexible, high-resilience foam seating; rigid foam insulation panels; microcellular foam seals and gaskets; durable elastomeric wheels and tires; automotive suspension bushings; electrical potting compounds; high performance adhesives; surface coatings; powder coatings; sealants; synthetic fibers (e.g., Spandex); carpet underlay; hard-plastic parts (e.g., for electronic instruments); and hoses. Polyurethane products can be recycled in various ways to remove them from the waste stream and to recapture some of the value inherent in the original material. Polyurethane recycle streams can result on job sites, from scrap PU or PIR during industrial production of flexible or rigid foam products and during building demolition. Examples of PU recycle methods include rebond to form carpet underlay, digestion via glycols to provide useful polyols, grinding PU products into powder for blending back into the original PU product and compression molding of scrap PU into useful articles. Thus, recycle or scrap PU streams exist that can be utilized in the practice of this invention.

Polyisocyanurates (PIRs)

Polyisocyanurates (PIRs) are digestible polymers useful herein. Polyisocyanurates are typically produced as a foam and used as rigid thermal insulation. It is commonly used in the building industry for building and pipe insulation. Scrap or recycle streams of PR are available from building demolition, from industrial production of PIR foams, scrap from the manufacture of new buildings or the retrofitting of new insulation into existing structures. Thus, recycle or scrap PIR streams exist that can be utilized in the practice of this invention.

Polyethers

Polyethers are digestible polymers useful herein. These polymers contain repeating units linked together by ether functional groups. Examples of such polyethers include polyethylene glycol (PEG), polypropylene glycol (PPG), polytetramethylene glycol (PTMG), and mixed PEG/PPG polymers. Since PU and PIR polymers utilize polyether polyols, the same recycle streams as exist for those polymers exist for polyethers. Additionally, it is conceivable that post-industrial streams exist for off-grade or scrap nonionic surfactants and polyether polyols that could be utilized for the practice of this invention.

Proteins

Proteins are digestible polymers useful herein. Proteins are naturally occurring polymeric materials made of amino acids linked together by peptide, i.e. amide groups. In other words, proteins are large biological molecules, or macromolecules, consisting of one or more long chains of amino acid residues. Proteins perform a vast array of functions within living organisms, including catalyzing metabolic reactions, replicating DNA, responding to stimuli, and transporting molecules from one location to another, and providing structure and mass to living organisms. Proteins differ from one another primarily in their sequence of amino acids, which is dictated by the nucleotide sequence of their genes, and which usually results in folding of the protein into a specific three-dimensional structure that determines its function and activity.

Proteins are also found combined with fats and are referred to as lipoproteins and with polysaccharides and are referred to as glycoproteins. The proteins are described separately herein from the man-made polyamides described above.

Proteins are found in a wide variety of agricultural materials, plants, and animals. Proteins and their use as recycle or waste streams are further described in "Proteins in Biomass Streams: A study commissioned by the Biorenewable Resources Platform (Platform Groene Grondstoffen), authored by Wim Mulder and dated April 2010, which is incorporated by reference herein in its entirety. Examples of proteins include keratin, collagen, milk proteins such as casein and whey, zein, silk and wool.

Keratin is a family of fibrous structural proteins. Keratin is the key structural material making up the outer layer of human skin. It is also the key structural component of hair and nails. Keratin monomers are assembled into bundles to form intermediate filaments, which are tough and insoluble and form strong unmineralized tissues found in reptiles, birds, amphibians, and mammals. A form of keratin called alpha-keratin is composed of alpha-coils and globular sections, and is the main component of hair, wool, nails, horns, and hooves. A form of keratin called beta-keratin, in which the protein strands are hydrogen-bonded into pleated sheets are found in the feathers, beaks and claws of birds and the and the claws, scales and shells of reptiles. Silk is also an example of keratin.

A digestible polymer source useful herein is avian, i.e. bird, feathers, which include the tougher outer or vane (also vaned, vein, or veined) feathers of birds and the softer inner, or juvenile feathers (also called down or down feathers). The poultry, both meat and egg producing, industries generate a large amount of waste feathers and down. Thus bird feathers such as chicken feathers, chicken down, duck feathers, duck down, goose feathers, goose down, turkey feathers, and turkey down, are an abundant and renewal source of digestible keratin polymers. See Bumla, N. A., et al., Process and Utilization of Feathers, Poultry Technology, Jul. 28, 2012; V. Saucedo-Rivalcoba, et al., (Chicken feathers keratin)/polyurethane membranes, Applied Physics A (2011) 104: 219-228; A. Ullah, et al., Bioplastics from Feather Quill, Biomacromolecules 2011, 12 3826-3832; and PCT Patent Application Publication No. WO 2014/023684 A1, to Nestec S. A., published Feb. 13, 2014; which are incorporated by reference herein in their entirety. Feather meal is a byproduct of processing poultry. It is made from poultry feathers by partially hydrolyzing them under elevated heat and pressure, and then grinding and drying them. Although total nitrogen levels are fairly high (up to 12%), the bioavailability of this nitrogen may be low. Feather meal is used in formulated animal feed and as an organic fertilizer. Feather meal is made through a process called rendering. Steam pressure cookers with temperatures over 140° C. are used to "cook" and sterilize the feathers. This partially hydrolyzes the proteins, which denatures them. It is then dried, cooled and ground into a powder for use as a nitrogen source for animal feed (mostly ruminants) or as an organic soil amendment. In certain instances feather meal can be particularly well suited for digestion as it can digest more completely than whole feathers.

Collagen is a fibrous, structural protein that is found in animal tissue, such as skin, bones, and tendons. The basic structure is a triple helix made up from three polypeptide chains, and has a common repeating unit of glycine, proline, and hydroxyproline. Collagen is readily available as a recycle stream from the livestock processing industry.

Milk proteins such as casein and whey are a major component of dairy products and represent a recycle stream from the dairy industry. Caseins are primarily phosphoproteins and are characterized by an open, random coil structure. Whey has a protein content of about 75-80% and is a by-product from cheese production and is rich in beta-lactoglobulin.

A variety of proteins are available from plant sources, including the important crops such as wheat, maize (corn), soy, potatoes, and other legumes such as peas. For example, a number of different proteins are found in maize (corn) including albumin, globulin, zein (a class of prolamine proteins), and glutelin. A number of proteins are also found in wheat, including albumin, globulin, and glutenins. Gluten is the main storage protein in wheat. Soy flour is made from roasted soybeans ground into a fine powder and contains 50 percent protein. Soy flour comes in three forms: natural or full-fat, defatted, and lecithinated. Natural or full-fat contains natural oils found in the soybean. Defatted has the oils removed during processing. Lecithinated has lecithin added. Soy flour is gluten-free, so yeast-raised breads made with soy flour are dense in texture. Soy grits are similar to soy flour except that the soybeans have been toasted and cracked into coarse pieces. Defatted soy flour is made entirely from defatted soy meal. Defatted soy flour is used as an ingredient and supplement to cereal products (wheat, corn, rice). It can be used in a wide variety of products including bread, weaning foods, cereals, cookies, muffins, cereals, cakes, pastas, and tortillas. It is currently being used worldwide by commercial processors. It is also a common ingredient in blended food aid products, such as Corn-Soy blend, Soy fortified wheat flour, et al. Defatted soy flour can also be fortified with various micronutrients and minerals. It should be recognized that soy flour is both a source of soy protein as well as carbohydrates. The nutrient data per 100 grams of uncooked defatted soy flour is reported as: moisture 9 g, Protein (N×6.25) moisture-free basis 52 g, ash 6 g, fat (petroleum ether) 1 g, fat (acid hydrolysis) 3 g, crude fiber 4 g, total dietary fiber 18 g, and total carbohydrates 30 g.

Wool is a fibrous protein fiber obtained from sheep and certain other animals, including cashmere from goats, mohair from goats, qiviut from muskoxen, angora from rabbits, and other types of wool from camelids.

Also, proteins can be obtained from aquatic sources such as fish, microalgae, and macroalgae (seaweed). Therefore, such materials are available from fish processing and seaweed farming.

Polysaccharides

Polysaccharides are digestible polymers useful herein. Polysaccharides are polymeric carbohydrate molecules composed of long chains of monosaccharide units bound together by glycosidic linkages. The polysaccharide chains can be linear or branched and include storage polysaccharides such as starch and glycogen, and structural polysaccharides such as cellulose and chitin. Polysaccharides include, e.g., polyglucosides (that is polymers of glucose) and sulphated polysaccharides. Examples of polyglucosides include starch, rayon, cellulose, cellophane, and chitin. Starch can be further characterized by the categories of helical amylose, amylopectin, and glycogen. Chitin is a polymeric material of N-acetylglucosamine, a derivative of glucose. Chitin is the main component of the cell walls of fungi, the exoskeletons of arthropods such as crustaceans (e.g., crabs, lobsters and shrimp) and insects, the radulae of molluscs, and the beaks and internal shells of cephalopods, including squid and octopuses. The structure of chitin is generally of crystalline nanofibrils or whiskers. Chitin is available as a recycle stream from the shellfish industry. An example of a sulphated polysaccharide is carrageenan, which is a linear polymer extracted from red edible seaweeds. Cellulose is an organic compound with the formula $(C_6H_{10}O_5)_n$," where "n" indicates the number of repeating formula units It is a polysaccharide consisting of a linear chain of several hundred to many thousands of $\beta(1\rightarrow 4)$ linked D-glucose units. Cellulose is an important structural component of the primary cell wall of green plants, many forms of algae and the oomycetes. Some species of bacteria secrete it to form biofilms. Cellulose is the most abundant organic polymer on Earth. The cellulose content of cotton fiber is 90%, that of wood is 40-50% and that of dried hemp is approximately 45%. Cellulose is mainly used to produce paperboard and paper. Smaller quantities are converted into a wide variety of derivative products such as cellophane, rayon and nitrocellulose. Cellulose for industrial use is mainly obtained from wood pulp, cotton and recycled paper products.

A polysaccharide useful herein is pectin. As described in sources such as Wikipedia, pectin is a structural heteropolysaccharide contained in the primary cell walls of terrestrial plants and was first isolated and described in 1825 by Henri Braconnot. Pectins are rich in galacturonic acid, and several distinct polysaccharides have been identified and characterised within the pectic group. Homogalacturonans are linear chains of α-(1-4)-linked D-galacturonic acid. Substituted galacturonans are characterized by the presence of saccharide appendant residues (such as D-xylose or D-apiose in the respective cases of xylogalacturonan and apiogalacturonan) branching from a backbone of D-galacturonic acid residues. Rhamnogalacturonan I pectins (RG-I) contain a backbone of the repeating disaccharide: 4)-α-D-galacturonic acid-(1,2)-α-L-rhamnose. Another structural type of pectin is rhamnogalacturonan II (RG-II), which is a less frequent, complex, highly branched polysaccharide. Rhamnogalacturonan II is classified by some authors within the group of substituted galacturonans since the rhamnogalacturonan ii backbone is made exclusively of D-galacturonic acid units. Isolated pectin has a molecular weight of typically 60,000-130,000 g/mol, varying with origin and extraction conditions. See U.S. Pat. No. 4,520,139, to Kennedy et al, issued May 28, 1985.

Polylactones and Polylactams

Polylactones and polylactams are digestible polymers useful herein. An example of a polylactone is a polymer made by the addition or ring-opening polymerization of caprolactone. An example of a polylactam is a polymer made by the polymerization of caprolactam. The polylactones are polyesters that contain multiple ester functional groups. Similarly, the polylactams are essentially polyamides, because they contain multiple amide functional groups as if they were instead derived from amino substituted carboxylic acids. Nylon-6, even though listed in the polyamide section, above, is essentially a polylactam made from the ring opening or addition polymerization or addition of caprolactam monomers. A possible source of recycled polylactone includes post-industrial scrap from polyurethane elastomer product manufacturing.

Glycols

Glycols suitable for use are well known. By "glycol," we mean a linear or branched, aliphatic or cycloaliphatic compound or mixture of compounds having two or more hydroxyl groups. Other functionalities, particularly ether or ester groups, may be present in the glycol. In preferred glycols, two of the hydroxyl groups are separated by from about 2 to about 20 carbons, preferably from about 2 to about 14 carbon atoms, and more preferably from about 2 to about 8 carbons. Note that ether linkages may be included in the carbon separation between hydroxyl groups, though the oxygen atoms are not included in the carbon count. Suitable glycols include, for example, ethylene glycol, propylene glycol, 1,3-propanediol, 1,2-butylene glycol, 1,3-butylene glycol, 1,4-butanediol, 2-methyl-1,3-propanediol, neopentyl glycol, glycerol, trimethylolpropane, 3-methyl-1,5-pentanediol, 1,4-cyclohexane-dimethanol, diethylene glycol, dipropylene glycol, triethylene glycol, 1,6-hexanediol, tripropylene glycol, tetraethylene glycol, polyethylene glycols (PEGs), polypropylene glycols (PPGs), erythritol, pentaerythritol, sorbitol, and block or random copolymer glycols of ethylene oxide and propylene oxide, and the like, and mixtures thereof. Preferably, the glycol is selected from ethylene glycol, propylene glycol, 2-methyl-1,3-propanediol, diethylene glycol, 3-methyl-1,5-pentanediol, neopentyl glycol, and polyethylene glycols with molecular weights less than about 600 (e.g., PEG 200 and PEG 400), and mixtures thereof. Propylene glycol is particularly preferred. In a preferred aspect, the glycol is a recycled glycol, especially propylene glycol and recycled diethylene glycol. Propylene glycol recovered from used deicing fluids is one example. In another preferred aspect, the glycol is a recycled ethylene glycol, which may be recovered from used engine antifreeze or coolant.

Aromatic Polyacid Source

The term "aromatic polyacid source" is used to designate that the material or source contains one or more aromatic acid moieties or groups. Chemical Structure 1, below, provides an illustration of an Aromatic Polyacid Source.

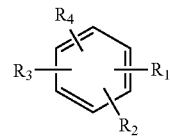

Chemical Structure 1

Where $R_1$ and $R_2$ are carboxylate groups; and $R_3$ and $R_4$ are selected from carboxylate group or hydrogen.

Chemical Structure 2, below provides another illustration of an Aromatic Polyacid Source.

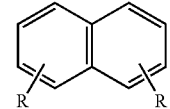

Chemical Structure 2

Where both R groups are carboxylic acid groups or alkyl ester groups.

Chemical Structure 3, below, provides another illustration of an Aromatic Polyacid Source.

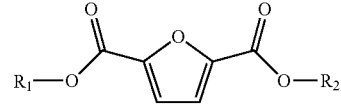

Chemical Structure 3

Where $R_1$ and $R_2$ are selected independently from either an alkyl group or hydrogen.

It should be noted that the aromatic polyacid source materials as described herein in this section are considered separate from and are a distinct component of the present invention, from the digestible polymers, as described separately in the "Digestible Polymers" section, above.

The aromatic polyacid source includes polyesters such as thermoplastic polyesters. These include polyesters polymers prepared by the reaction of one or more difunctional and/or multifunctional aromatic carboxylid acids with one or more difunctional hydroxyl compounds and/or multifunctional hydroxyl compounds.

Examples of materials that contain aromatic polyacid groups suitable for the practice of the invention include phthalic acid, phthalic anhydride, dimethyl phthalates, dialkyl phthalates, terephthalic acid, dimethyl terephthalates, dialkyl terephthalate, isophthalic acid, dimethyl isophthalates, dialkyl isophthalates, DMT bottoms (for example, as described in U.S. Pat. No. 5,075,417; U.S. Pat. No. 4,897,429; U.S. Pat. No. 3,647,759; U.S. Pat. No. 4,411,949; U.S. Pat. No. 4,714,717; and U.S. Pat. No. 4,897,429), trimellitic acid, trimellitic anhydride, trimethyl trimellitate, naphthalene dicarboxylic acid, pyromellitic anhydride, 2,5-furandicarboxylic acid, dialkyl 2,5-furandicarboxylate, pyromellitic acid, dialkyl naphthalene dicarboxylate, and mixtures thereof.

Also, the term "terephthalic acid" is intended to include terephthalic acid itself and residues thereof as well as any derivative of terephthalic acid, including its associated acid halids, esters, half-esters, salts, half-stats, anhydrides, mixed anhydrides, or mixtures thereof or residues thereof useful in a reaction process with a diol to make a polyester.

Aromatic polyacid sources may also be obtained from thermoplastic polyesters. Thermoplastic polyesters suitable for use are well known in the art. They are condensation polymers produced from the reaction of glycols and aromatic dicarboxylic acids or acid derivatives. Examples include polyethylene terephthalate (PET), polybutylene terephthalate (PBT), polytrimethylene terephthalate (PTT), glycol-modified polyethylene terephthalate (PETG), copolymers of terephthalic acid and 1,4-cyclohexanedimethanol (PCT), copolymers of 2,5-furandicarboxylic acid or dialkyl 2,5-furandicarboxylates and at least one glycol, PCTA (an isophthalic acid-modified PCT), copolymers of naphthalene dicarboxylic acid or dialkyl naphthalene dicarboxylate and the like, and mixtures thereof.

Suitable thermoplastic polyesters include virgin polyesters, recycled polyesters, or mixtures thereof. Polyethylene terephthalate (PET) is particularly preferred, especially recycled polyethylene terephthalate (rPET), virgin PET, and mixtures thereof. For more examples of suitable thermoplastic polyesters, see U.S. Pat. Appl. Publ. No. 2009/0131625, the teachings of which are incorporated herein by reference.

Recycled polyethylene terephthalate suitable for use in making the inventive polyester polyols can come from a variety of sources. The most common source is the post-consumer waste stream of PET from plastic bottles or other containers. The rPET can be colorless or contain dyes (e.g., green, blue, brown, or other colors) or be mixtures of these. A minor proportion of organic or inorganic foreign matter (e.g., paper, other plastics, glass, metal, etc.) can be present. A desirable source of rPET is "flake" rPET, from which many of the common impurities present in scrap PET bottles have been removed in advance. Another desirable source of rPET is pelletized rPET, which is made by melting and extruding rPET through metal filtration mesh to further remove particulate impurities. Because PET plastic bottles are currently manufactured in much greater quantity than any recycling efforts can match, scrap PET will continue to be available in abundance. Other sources of PET include, PET textiles and PET carpeting, such as recycled PET textiles and recycled PET carpeting. For example, recycled PET polyester carpet including polyolefin backing, calcium carbonate filler, and latex adhesive, assuming an approximate PET composition of 90% of the carpet, is a useful source material to prepare the digested intermediate.

Polytrimethylene terephthalate (PTT) is another useful polyaromatic source, and like PET, can be obtained from PTT textiles and PTT carpeting, such as recycled PTT textiles and recycled PTT carpeting. For example, recycled PTT polyester carpet including polyolefin backing, calcium carbonate filler, and latex adhesive, assuming an approximate PTT composition of 90% of the carpet, is a useful source material to prepare the digested intermediate.

Other useful polyaromatic sources are polyesters made from polyaromatics and rigid diols such as cycloalkane diols, examples of such rigid diols including 2,2,4,4-tetramethyl-1,3-cyclobutanediol, 1,3-cyohexane diol, 1,4-cyclohexane diol, 1,3-cyclohexanedimethanol, and 1,4-cyclohexanedimethanol. Such examples include terephthalate copolyesters of 2,2,4,4-tetramethyl-1,3-cyclobutanediola, and also polyesters which also contain flexible diols, such as C2-C6 linear or branched aliphatic diols. Examples of these polyesters include, for example Eastman Tritan materials from post-consumer recycle of water bottles See, also, U.S. Patent Application No. US 2013/0072628 A1, to Crawford et al., published Mar. 21, 2013; and D. R. Kelsey et al., *High Impact, Amorphous Terephthalate Copolyesters of Rigid 2,2,4,4-Tetramethyl-1,3-cyclobutanediol with Flexible Diols*, Macromolecules, 2000, 33, 5810-5818; which are incorporated by reference herein in their entirety.

Hydrophobes and Nonionic Surfactants

The polyester polyols of this invention may also comprise hydrophobes, nonionic surfactants, and mixtures thereof. Hydrophobes include triglycerides and modified triglycerides, fatty acids, fatty acid esters, dimer fatty acids, fatty diacids, vegetable oils and modified vegetable oils (for example as described in U.S. Pat. No. 5,922,779, U.S. Pat. No. 6,359,022, U.S. Pat. No. 6,664,363, and WO 2013/154874A1); castor oil (for example, as described in WO 2013/154874A1); modified or derivatized polyterpenes; modified cashew nut shell oil; cardanol; derivatives of cardanol; Diels Alder or ene reaction modified polyols (for example, as described in WO 2013/109834); and tall oil fatty acids (for example, as described in U.S. Pat. No. 5,075,417 and U.S. Pat. No. 4,897,429). The aromatic polyester polyols may further comprise nonionic surfactants or reactants (for example, as described in U.S. Pat. No. 4,529,744, WO 9919377 and WO 2009045926).

Examples of triglycerides suitable for the practice of this invention include soybean oil, animal tallow, fish oil, canola oil, castor oil, tung oil, linseed oil, corn oil, recycled cooking oil, sunflower oil, palm oil, peanut oil, palm kernel oil, cottonseed oil, coconut oil, and safflower oil.

Examples of fatty acids suitable for the practice of this invention include linoleic, myristic, palmitic, caproic, caprylic, capric, 2-ethyl hexanoic, lauric, stearic, oleic, linolenic, ricinoleic, tall oil, and mixtures thereof. The alkyl esters of these fatty acids and mixtures of these alkyl esters thereof are also suitable examples for the practice of this invention.

Examples of fatty diacids suitable for the practice of this invention include azelaic acid; sebacic acid; dodecanedioic acid; tetradecanedioic acid; hexadecanedioic acid; octadecanedioic acid; nonene dioic acid; decenedioic acid, dodecenedioic acid; tetradecenedioic acid; hexadecenedioic acid; octadecenedioic acid; eicosendioic acid; eicosandioic acid; docosandioic acid; tetracosandioic acid; tetracosendioic acid; and the like and mixtures thereof.

Examples of nonionic surfactants include block copolymers of ethylene oxide with either propylene oxide, butylene oxide, or mixtures of propylene oxide with butylene oxide. See "nonionic Surfactants: Polyoxyalkylene Block Copolymers", (Surfactant Science Series, Book 60, CRC Press), 1996, Vaughn Nace, ed. And "Nonionic Surfactants: Organic Chemistry" (Surfactant Science Series Book 72), 1997 Nico M. van Os., ed. It is well known that initiators are used to initiate such block copolymers. Suitable initiators include glycols; monols; fatty alcohols; alkyl phenols; phenol; styrenated phenols; bisphenols; triols; and tetrols. An additional nonionic surfactant suitable for use as a reactant or additive includes ethoxylated or alkoxylated castor oil.

Catalysts

Catalysts suitable for making the digested intermediate are well known (see, e.g., K. Troev et al., *J. Appl. Polym. Sci.* 90 (2003) 1148). In particular, suitable catalysts comprise titanium, zinc, antimony, germanium, zirconium, manganese, or other metals. Specific examples include titanium alkoxides (e.g., tetrabutyl titanate), titanium(IV) phosphate, zirconium alkoxides, zinc acetate, lead acetate, cobalt acetate, manganese(II) acetate, antimony trioxide, germanium oxide, or the like, and mixtures thereof. Catalysts that do not significantly promote isocyanate reaction chemistries are preferred. The amount of catalyst used is typically in the range of 0.005 to 5 wt. %, preferably 0.01 to 1 wt. %, more preferably 0.02 to 0.7 wt. %, based on the total amount of polyol being prepared.

The hydrolysis and chemolysis of the digestible polymer can be catalyzed by the use of enzymes such as proteases; lipases; amylases; maltases; sucrases; lactases; esterases; hydrolases; amidases; glycosidases; glycoside hydrolases; peptidases and the like and mixtures thereof. Subsequent reaction of the resulting hydrolysis or chemolysis products with the digested intermediate may then be facilitated by enzymes such as lipases; amidases and esterases.

The reaction of the digestible polymer with the digested intermediate can also be catalyzed by the use of acids or bases, including carboxylic acids.

Processes, Properties and Compositions

The present invention provides a means for recycling both the aromatic acid source and the digestible polymer to provide a polyester polyol having a high recycle content. The recycle content of the resultant polyester polyol can have a wide range of recycle content, but those having a recycle content of about 50% by weight or more would be particularly attractive.

With respect to recycle streams, when the material is nylon-6, nylon-6,6, or PTT carpet, the fibers typically originate as post-industrial off-grade or defective recycle carpet, greige goods, or fiber products and post-consumer recycle carpet. In the case of post-consumer recycled carpet, the carpet is typically collected by carpet un-installers for use as a recycle stream. This stream has more contaminants such as dirt, pet hair, mold and the like than a post-industrial recycle carpet stream, and may require a washing step in conventional recycling schemes prior to use as a recycled nylon-6, nylon-6,6, or PTT stream. Hence, a process, as in the present invention, that circumvents the need for a wash step would represent an improvement in sustainability.

When the recycle stream is a polycondensation or addition polymer textile or fabric, or fibers, the material typically originates as post-industrial off-grade or scrap, and can contain dyes and other contaminants. Post industrial off-grade might originate from incorrectly dyed fabric or incorrectly woven textiles. Post industrial scrap can originate from leftover fabric that results from cutting fabric during the manufacture of clothing, carpet, furniture, shoes, curtains, and other textile based articles that use polycondensation or addition polymer textiles or fabrics. Post consumer recycling of polycondensation or addition polymer textiles or fabrics can occur by utilizing worn-out clothing from apparel and uniform manufacturers and retailers as well as government agencies, hospitals and clinics, schools, sports clubs, and other entities.

The thermoplastic polyester and glycol are heated, optionally in the presence of a catalyst, to give a digested intermediate. The digested intermediate will commonly be a mixture of glycol reactant, glycol(s) generated from the thermoplastic polyester, terephthalate oligomers, and other glycolysis products. For example, when PET or rPET is the thermoplastic polyester, the digested intermediate will include a mixture of glycol reactant, ethylene glycol (generated from the PET or rPET), bis(2-hydroxyalkyl) terephthalate ("BHAT"), higher PET oligomers, and other glycolysis products. Similar digested mixtures in various forms have been made and characterized previously (see, e.g., D. Paszun et al., *Ind. Eng. Chem. Res.* 36 (1997) 1373 and N. Ikladious, *J. Elast. Plast.* 32 (2000) 140). Heating is advantageously performed at temperatures within the range of 80° C. to 260° C., preferably 130° C. to 240° C., more preferably 150° C. to 230° C., and most preferably 160° C. to 220° C.

More specifically, in the context of the present invention, glycolysis refers to the reaction of the hydroxyl group of a digested aromatic polyacid source, e.g., a thermoplastic polyester intermediate with a digestible polymer in a manner to reduce the molecular weight of the digestible polymer thereby providing a polyol that is liquid at temperatures between 20° C. and 120° C.

In one aspect, when the thermoplastic polyester is polyethylene terephthalate, the digested intermediate comprises a glycol or mixture of glycols and a terephthalate component. The glycols and terephthalate components must be digested via a transesterification reaction and this digestion reaction is performed by heating the thermoplastic polyester, glycol(s), and any catalyst at least until the mixture liquefies and particles of the thermoplastic polyester are no longer apparent at the temperature of reaction. Reaction times range from about 30 minutes to about 16 hours, more typically 1 to 10 hours, even more typically 3 to 8 hours, and will depend on the reaction temperature, source of the thermoplastic polyester, the particular glycol reactant used, mixing rate, desired degree of depolymerization, and other factors that are within the skilled person's discretion.

The molar ratio of glycol to aromatic polyacid source is at least 0.8, preferably 2.0 to 6.0, more preferably 2.5 to 4.5. When the glycol/aromatic polyester source molar ratio is below about 2.0, the products are often solids at room temperature or too viscous to be practical for use as conventional polyols for polyurethane applications, however, for the purpose of digesting digestible polymers at elevated temperatures, glycol to thermoplastic polyester ratios between 0.8 and 2.0 are acceptable. On the other hand, when the glycol/aromatic polyester source molar ratio is greater than about 6, the hydroxyl numbers of the resulting digested digestible polymer-based polyols tend to exceed the practical upper limit of about 800 mg KOH/g.

In a second reaction step, the digested intermediate described above is reacted with a digestible polymer to give the inventive polyester polyol.

The reaction between the digested intermediate and the digestible polymer is performed under conditions effective to promote reaction between one or more functional groups of the digestible polymer and hydroxyl groups present in the digested intermediate.

The weight percent of digestible polymer in the resulting polyester product after digestion is from 1% to 75%, preferably from 3% to 60%, most preferably from about 5% to about 45%.

As long as some digestible polymer is used to make the polyol, one or more other digestible polymers can also be included. Mixtures of digestible polymers can be used.

In another aspect, the polyester polyol is made in a single step, or one pot reaction, by reacting the aromatic polyacid source, glycol, and digestible polymer under conditions effective to produce the polyol. As with polyols made using the two-step process, the weight percent of digestible polymer in the resulting polyester product after digestion is from 1% to 75%, preferably from 3% to 60%, most preferably from 5% to 45%, the molar ratio of glycol to aromatic polyester source is at least 0.8, and the resulting polyol has a hydroxyl number within the range of 10 to 800 mg KOH/g. When the single-step process is used, it is preferred to utilize a condensation system that returns glycols to the reaction vessel while allowing removal of water, as removal of too much glycol can result in cloudy or opaque polyols. Examples III and IX below illustrates the single-step process.

The inventive polyester polyols have hydroxyl numbers within the range of 10 to 800 mg KOH/g, preferably 25 to 500 mg KOH/g, more preferably 35 to 400 mg KOH/g, and even more preferably 50 to 400 mg KOH/g. Hydroxyl number can be measured by any accepted method for such a determination, including, e.g., ASTM E-222 ("Standard Test Methods for Hydroxyl Groups Using Acetic Anhydride Acetylation").

The inventive polyols preferably have average hydroxyl functionalities (i.e., the average number of —OH groups per molecule) within the range of 1.5 to 5.0, more preferably 1.8 to 4.5, and most preferably 2.0 to 4.0.

The inventive polyols are flowable liquids at temperatures between 20° C. and 125° C. Preferably, the polyols have viscosities measured at between 25° C. and 125° C. of less than about 20,000 cP. In some embodiments, the polyols have a viscosity at 25° C. less than about 20,000 cP. In other embodiments, the polyols have a viscosity at 25° C. less than about 10,000 cP. In yet other embodiments, the polyols have a viscosity at 125° C. less than about 5000 cP. However, polyols outside these viscosity ranges can also be useful.

Viscosity can be determined by any industry-accepted method. It is convenient to use, for instance, a Brookfield viscometer (such as a Brookfield DV-III Ultra rheometer) fitted with an appropriate spindle, and to measure a sample at several different torque settings to ensure an adequate confidence level in the measurements.

The polyols preferably have low acid numbers. Urethane manufacturers will often require that a polyol have an acid number below a particular specification. Low acid numbers can be ensured by driving the condensation step (with digestible polymer) to the desired level of completion or by adding an acid scavenger (e.g., Cardura™ E10P glycidyl ester manufactured by Momentive) at the conclusion of the condensation step. Preferably, the polyols have an acid number less than 30 mg KOH/g, more preferably less than 10 mg KOH/g, and most preferably less than 5 mg KOH/g. As suggested above, it is acceptable practice to adjust acid numbers if necessary for a particular application with an acid scavenger such as, for example, an epoxide derivative, and this treatment can be performed by the manufacturer, distributor, or end user.

In the case of polyester polyols prepared using PU or PIR digestible polymers, small amounts of toluene diamine (TDA), methylene diphenyl amine (MDA) or polymeric methylene diphenyl amine (PMDA) may be formed. As these substances are hazardous materials, it is desirable to reduce or eliminate their presence in the resulting polyester polyols. It is believed that this may be accomplished by introducing small amounts of an amine scavenger such as, for example, an alkylene oxide, a glycidyl ether, an epoxy-derivative such as epoxidized soybean oil, an isocyanate or polyisocyanate derivative into the resulting polyester polyol concurrent with heating and stirring to achieve reaction between the TDA, PMDA or MDA an the amine scavenger, thereby reducing the content of these hazardous substances in the polyester polyols derived from PU and PIR digestible polymers.

An advantage of the polyester polyols is their reduced reliance on bio- or petrochemical sources for raw material. Preferably, the polyols include greater than 10 wt. %, more preferably greater than 25 wt. %, most preferably greater than 50 wt. % of recycle content. A preferred range for the recycle content is 25 to 99.9 wt. %. By "recycle content," we mean the combined amounts of recycled thermoplastic polyester and any recycled glycol or digestible polymer. Some glycols, such as propylene glycol or ethylene glycol, are available as recovered or recycled materials. For instance, propylene glycol is used in deicing fluids, and after use, it can be recovered, purified, and reused. Additionally, recycled ethylene glycol may be obtained from recovered engine antifreeze or engine coolant. Preferably, the digestible polymer is prepared or obtained from renewable resources or post-consumer or post-industrial recycled sources. Recycle content can be calculated, for instance, by combining the masses of recycled thermoplastic polyester and any recycled glycol or recycled digestible polymer, dividing this sum by the total mass of reactants (glycols, thermoplastic polyester, and digestible polymer), and then multiplying the result by 100.

A desirable polyol attribute is the absence of settling, particularly upon prolonged storage. When settling is substantial, the polyol might have to be filtered, stirred, stirred with heating or otherwise treated to remove or redissolve the solids content; this is preferably avoided. Preferred inventive polyols exhibit no settling or only a slight degree of settling, and more preferred polyols exhibit no evidence of settling.

In a specific aspect, the invention relates to a process which comprises: (a) heating virgin PET, recycled PET, or a mixture thereof with propylene glycol in the presence of a zinc or titanium catalyst to give a digested intermediate; and (b) condensing the intermediate with a digestible polymer to give the polyester polyol; wherein the weight percent of digestible polymer in the resulting polyester product after digestion is from 1% to 75%, preferably from 3% to 60%, most preferably from about 5% to about 45%, the molar ratio of glycol to PET is within the range of 2.5 to 4.5, and the polyol has a hydroxyl number within the range of 25 to 500 mg KOH/g, a viscosity less than 20,000 cP between 25° C. and 90° C., and a recycle content as defined herein greater than 25 wt. %.

Products Prepared from Polyols

The inventive polyester polyols can be used to formulate a wide variety of polyurethane products. By adjusting the proportion of digestible polymer used, a desired degree of polyol hydrophobicity can be "dialed in." The ability to control hydrophobicity is particularly valuable in the coatings industry. The polyols can be used for cellular, microcellular, and non-cellular applications including flexible foams, rigid foams (including polyisocyanurate foams), urethane dispersions, coatings, powder coatings, adhesives, sealants, and elastomers. The resulting polyurethanes are potentially useful for automotive and transportation applications, building and construction products, marine products, packaging foam, flexible slabstock foam, carpet backing, appliance insulation, cast elastomers and moldings, footwear, biomedical devices, and other applications.

Further, the inventive polyester polyols may be derivatized to form mono-, di- and polyacrylates via esterification or transesterification with acrylic acid or methacrylic acid-derived raw materials. Examples of (meth)acrylation raw materials suitable for forming (meth)acrylate derivatives of the inventive polyester polyols include acryloyl chloride, methacryloyl chloride, methacrylic acid, acrylic acid, methyl acrylate, methyl methacrylate, and the like, or mixtures thereof. Such (meth)acrylate-derivatized inventive polyester polyols are useful for radiation or UV-cure coating formulations or applications. Isocyanate prepolymers of the inventive polyester polyols may be derivatized to form urethane (meth)acrylates via reaction with hydroxyethyl (meth)acrylate. The resulting urethane acrylates may also be used in radiation or UV-cure coating formulations or applications.

In a particular aspect, the invention relates to aqueous polyurethane dispersions made from the inventive polyester polyols. We found that the digestible polymer modified polyols are readily formulated into aqueous polyurethane dispersions having a desirable balance of properties, including high solids and low viscosities, and a low tendency to settle. Numerous ways to formulate aqueous polyurethane dispersions are known and suitable for use. Preferably, the polyurethane dispersion is made by emulsifying an isocyanate-terminated prepolymer in water with the aid of an emulsifying agent. Water, a water-soluble polyamine chain extender, or a combination thereof may be used to react with the emulsified prepolymer. The prepolymer is preferably made by reacting an inventive polyester polyol, a hydroxy-functional emulsifier, one or more auxiliary polyols, and one or more polyisocyanates. The aqueous polyurethane dispersions are preferably used to formulate water-borne coatings, adhesives, sealants, elastomers, and similar urethane products, and they are particularly valuable for reducing reliance on solvents. For instance, the dispersions can be used to formulate low- or zero-VOC compositions.

Polyisocyanates suitable for use in making the prepolymers are well known; they include aromatic, aliphatic, and cycloaliphatic polyisocyanates. Examples include toluene diisocyanates (TDIs), MDIs, polymeric MDIs, naphthalene diisocyanates (NDIs), hydrogenated MDIs, trimethyl- or tetramethylhexamethylene diisocyanates (TMDIs), hexamethylene diisocyanate (HDI), isophorone diisocyanates (IPDIs), cyclohexane diisocyanates (CHDIs), xylylene diisocyanates (XDI), hydrogenated XDIs, and the like. Aliphatic diisocyanates, such as hexamethylene diisocyanate and isophorone diisocyanates are particularly preferred.

Auxiliary polyols suitable for use are also well known. They include polyether polyols, aliphatic polyester polyols, aromatic polyester polyols, polycarbonate polyols, glycols, and the like. Preferred auxiliary polyols have average hydroxyl functionalities within the range of 2 to 6, preferably 2 to 3, and number average molecular weights within the range of 500 to 10,000, preferably 1,000 to 8,000. Preferred polyester polyols are condensation products of aromatic or aliphatic diacids and diols or triols (e.g., ethylene glycol, propylene glycol, 2-methyl-1,3-propanediol, 3-methyl-1,5-pentanediol, 1,4-butanediol, neopentyl glycol, glycerin, trimethylolpropane, 1,4-cyclohexanedimethanol, bisphenol A ethoxylates), especially diols.

A hydroxy-functional emulsifier is also used to make the polyurethane dispersions. The role of this component is to impart water-dispersibility to the prepolymer, usually upon its combination with water and a neutralizing agent, such as an acid or base reactant. Thus, in one aspect, the hydroxy-functional emulsifier is an acid-functional diol such as dimethylolpropionic acid (DMPA) or dimethylolbutanoic acid (DMBA). The acid functionality in the resulting prepolymer allows for neutralization with an amine or other basic reactant to generate a water-dispersible urethane. The hydroxy-functional emulsifier can also be an amine, such as N-methyldiethanolamine. Neutralization of the resulting prepolymer with an acidic reagent renders it water dispersible. In other aspects, the hydroxy-functional emulsifier is nonionic, e.g., a polyethylene glycol monomethyl ether. In another aspect, the hydroxy-functional emulsifier may be a monol- or diol-functionalized poly(ethylene oxide), such as for example Ymer™ N120 dispersing monomer (product of Perstorp), polyethylene glycols, or the methyl ether of polyethylene glycol. Additionally, non-reactive, so-called "external emulsifiers," such as the triethanolamine salt of dodecylbenzene sulfonic acid, may be included in the aqueous phase to assist in the emulsification and stabilization of the prepolymer and resulting polyurethane dispersion.

In certain aspects, a chain terminator may be used to control the molecular weight of polyurethane polymer contained within the aqueous polyurethane dispersion. Monofunctional compounds, such as those containing hydroxyl, amino, and thio groups that have a single active hydrogen-containing group, are suitable chain terminators. Examples include alcohols, amines, thiols, and the like, especially primary and secondary aliphatic amines.

Chain extenders can also be included in making the polyurethane dispersion. In some aspects, the chain extender is added in an amount sufficient to react 5 to 105 mole % of free NCO groups present. Suitable chain extenders contain at least two functional groups that are capable of reacting with isocyanates, e.g., hydroxyl, thio, or amino groups in any combination. Suitable chain extenders include, for example, diols (ethylene glycol, propylene glycol, diethylene glycol, neopentyl glycol, 1,4-butanediol, 2-methyl-1,3-propanediol, 3-methyl-1,5-pentanediol, 1,4-cyclohexanedimethanol, and the like), di- and polyamines (ethylenediamine, diethylenetriamine, Jeffamine® T-403, Jeffamine® D-230, Jeffamine® ED-2001, Jeffamine® ED-600, Jeffamine® ED-900, 1,6-hexamethylenediamine, butylenediamine, hydrazine, piperazine, N-hydroxyethyl ethylenediamine) alkanolamines (ethanolamine, diethanolamine, N-methyl diethanolamine, and the like), dithiols, and the like. Diol chain extenders are preferably added during the preparation of the prepolymer, and prior to emulsification in water.

For more examples of suitable approaches for preparing aqueous polyurethane dispersions, see U.S. Pat. Nos. 5,155,163; 5,608,000; 5,763,526; 6,339,125; 6,635,723, 7,045,573; and 7,342,068, the teachings of which are incorporated herein by reference.

Coatings

The polyester polyols of the present invention are useful for making coatings. A coating is a covering that is applied to the surface of an object, which usually referred to as the substrate. The coatings typically comprise from about 1% to about 95%, by weight of the polyester polyol, preferably from about 2% to about 90% by weight of the polyester polyol, and more preferably from about 5% to about 80% by weight of the polyester polyol. The optimum weight percentage of the polyester polyol can be determined by one of skill in the art to obtain the desired property of the coating both before and after application to the substrate. Both liquid coatings and powder coatings can be made with the polyols of the present invention. Examples of liquid coatings include polyurethane coatings. These liquid coatings can include additional components such as catalysts, flow and leveling agents, surface modifying additives, wetting agents, dispersing agents, foam-control agents, solvents, crosslinking additives, co-blended resins to modify properties, pigments and colorants, and degassing agents.

Powder coatings provide an important alternative to liquid coatings. These coatings can be prepared from resins, pigments, and additives. The powder is applied to a substrate, usually metal, and fused to form a continuous film by baking the coated metal, or by applying the powder coating to a heated substrate. The powder coatings typically have a glass transition temperature, $T_g$, greater than or equal to 45° C., preferably greater than or equal to 50° C., and more preferably greater than or equal to 55° C. The powder coatings also typically have a melting point greater than or equal to 45° C., preferably greater than or equal to 50° C., and more preferably greater than or equal to 55° C. The glass transition temperature and the melting point of the powder coating can be adjusted by the selection of the polyester polyol or polyols incorporated, as well as the weight percentage of the polyol or polyols in the coating. It is highly desirable to adjust the glass transition temperature and melting point such that the powder coating remains as a free flowing powder at room temperature and elevated storage conditions, such as for example in a hot warehouse, but also readily melts to form a uniform coating on a substrate that has either been preheated before application of the powder coating or that is subsequently baked after application of the powder coating. While it is important to maintain a high enough glass transition temperature and melt temperature to prevent sintering, it is desirable to simultaneously tune the powder coating such that the optimal melt flow and cross-linking temperature is as low as possible, which results in a lower, narrower process window for films. This lower temperature is advantageous from an energy savings standpoint to the applicator. Additives are an important ingredient in the formulation of powder coatings. For the most part, additives perform the same functions in powder coatings as in liquid coatings. With the exception of wetting, dispersing and foam-control agents, many of the same additives used in liquid coatings are also used in powders. The powder coatings can comprise additional components such as cross-linking agents, flow control agents, degassing agents, catalysts, and pigmenting materials. The powder coatings can be applied to a metal substrate using conventional techniques known in the art such as electrostatic spraying. The metal substrate can either be preheated before application of the powder coating or baked after the application of the powder coating to thermally set the coating.

See U.S. Pat. No. 5,637,654, to Panandiker et al, issued Jun. 10, 1997; U.S. Pat. No. 4,197,353, to Tobias et al, issued Apr. 8, 1980; PCT Patent Application No. WO 2011/138432 A1, to DSM IP Assets, B.V., published Nov. 10, 2011; and "Organic Coatings Science and Technology", 3rd Ed., Wiley, 2007, Z. Wicks, Jr., F Jones, S. P. Pappas, D. A. Wicks, Chapter 28.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

"Recycle content" as used herein (wt. %) is determined by combining the masses of recycled glycol, recycled aromatic polyacid source, recycled hydrophobe, and recycled digestible polymer, and dividing this sum by the total mass of reactants, and then multiplying the result by 100.

Hydroxyl numbers and acid numbers are determined by standard methods (ASTM E-222 and ASTM D3339, respectively). Viscosities are measured at 25° C. using a Brookfield DV-III Ultra rheometer with spindle #31 at 25%, 50%, and 75% torque, with 50% torque being the usual torque setting. Alternatively, depending on the viscosity of the sample, viscosities can also be measured at other temperatures, including up to about 50° C. or higher. Also, viscosities can be determined on diluted samples. Color, clarity, and degree of settling are evaluated visually.

Examples I-VII provide procedures for carrying out the indicated digestion process on an aromatic polyacid source to produce a digested intermediate which can be utilized for further digesting the various digestible polymers of the present invention. Examples VIII-XXV provide procedures for carrying out the further digestion of various digestible polymers. Example XXVI provides a procedure for making polyurethane coatings from the polyols. Example XXVII provides a procedure for making powder coatings from the polyols. Examples XXVIII and XXIX provide procedures for making rigid polyisocyanurate foams. Table 1 summarizes physical characteristics data for the digestion product from various aromatic polyacid sources. Table 2 summarizes physical characteristics data for the digestion products of various digestible polymers. Table 3 summarizes physical characteristics data on polyurethane coatings made from the polyester polyols from the digestible polymers of the present invention.

Example I: Preparation of Digested Intermediate from an Aromatic Polyacid Source (Recycled PET)

The following relative amounts of materials were used—(1.0 mole rPET/2.8 mole PG/0.46 mole dimer fatty acid). A 5 liter reactor equipped with an overhead mixer, condenser, heating mantle, thermocouple, and nitrogen inlet was charged with titanium tetrabutoxide (0.1% by wt.), recycled polyethylene terephthalate pellets (960 g, 5 moles), and propylene glycol (1065.2 g, 14 moles). The mixture was heated with stirring to about 130° C. Stirring was then set to 60 rpm, and heating continued until the reactor contents reached 200° C. The mixture was heated until no particles of recycled PET remained (about 4 hr). When the digestion reaction was considered complete, the mixture was cooled to about 100° C. Dimer fatty acid (Croda Pripol™1017, 1311.7 g, 2.3 moles) was added, while the mixing rate was increased to 200 rpm. When the addition was complete, a Dean-Stark trap was introduced between the reactor and condenser, the mixture was then heated to 170° C. The temperature was slowly increased over time to 185° C. depending on how fast water was collected in the Dean Stark trap. Water generated in the condensation reaction was removed until roughly the theoretical amount was removed. When the reaction was complete, the digested intermediate was allowed to cool to 100° C. and then decanted from the reactor. Any residual solids were removed by filtration through cheesecloth. The resulting transparent amber digested intermediate had an OHV (hydroxyl value) of 380 mg KOH/g of sample and a viscosity at 25° C. of 3097 cP (centipoise). See Acid Source Example 1 in Table 1.

Example II: Preparation of Digested Intermediate from an Aromatic Polyacid Source (Recycled PET Carpet)

A 2000 mL resin kettle equipped with an overhead mixer, Vigreux column, short path condenser head with distillation collection flask, heating mantle, thermocouple, and nitrogen inlet was charged with 152.80 g of recycled propylene glycol, 142.80 g of recycled PET polyester carpet including polyolefin backing, calcium carbonate filler, and latex adhesive, assuming an approximate PET composition of 90% of the carpet, and 0.58 g titanium tetrabutoxide (~0.1% by wt.) and heated with a stirring rate of 150 RPM and nitrogen flow at 0.3SCFH to 200° C. for 20 hours. After about 5 hours, the recycled PET polyester textile had completely dissolved and appeared to be completely digested. The mixture was heated overnight to ensure no particles of recycled PET carpet remained. The mixture was then cooled to about 100° C. 190.88 g of Dimer Fatty Acid (Croda Pripol 1017) was added, while the mixing rate was increased to 350 rpm. When the addition was complete the mixture was then heated to 200° C. and nitrogen was increased to 1.0SCFH. Water generated in the condensation reaction was collected in the distillation flask until roughly the theoretical amount was removed. When the reaction was complete, the reactor was allowed to cool to 100° C. and then poured into a jar. Undigested polyolefin backing was removed by forceps and the mixture of polyol with calcium carbonate was run through a glass fritted disc filter size 'F' (<5 μm) at about 80° C. The resulting transparent dark amber polyol had an OHV (hydroxyl value) of 352.0 mg KOH/g of sample and a viscosity at 25° C. of 3000 cP (centipoise). See Acid Source Example 2 in Table 1.

Example III: Preparation of Digested Intermediate from an Aromatic Polyacid Source (Recycled PTT Carpet)

A 2000 mL resin kettle equipped with an overhead mixer, Vigreux column, short path condenser head with distillation collection flask, heating mantle, thermocouple, and nitrogen inlet was charged with 149.47 g of recycled propylene glycol, 150.03 g of recycled PTT polyester carpet including polyolefin backing, calcium carbonate filler, and latex adhesive, assuming an approximate PTT composition of 90% of the carpet, and 0.58 g titanium tetrabutoxide (~0.1% by wt.) and heated with a stirring rate of 150 RPM and nitrogen flow at 0.3SCFH to 200° C. for 20 hours. After about 5 hours, the recycled PTT polyester textile had completely dissolved and appeared to be completely digested. The mixture was heated overnight to ensure no particles of recycled PTT carpet remained. The mixture was then cooled to about 100° C. 186.72 g of Dimer Fatty Acid (Croda Pripol 1017) was added, while the mixing rate was increased to 350 rpm. When the addition was complete the mixture was then heated to 200° C. and nitrogen was increased to 1.0 SCFH. Water generated in the condensation reaction was collected in the distillation flask until roughly the theoretical amount was removed. When the reaction was complete, the reactor was allowed to cool to 100° C. and then poured into a jar. Undigested polyolefin backing was removed by forceps and the mixture of polyol with calcium carbonate was run through a glass fritted disc filter size 'F' (<5 μm) at about 80° C. The resulting transparent dark amber polyol had an OHV (hydroxyl value) of 371.1 mg KOH/g of sample and a viscosity at 25° C. of 2307 cP (centipoise). See Acid Source Example 3 in Table 1.

Example IV: Preparation of Digested Intermediate from an Aromatic Polyacid Source (Recycled PET Textile)

A 500 mL reactor equipped with an overhead mixer, Vigreux column, short path condenser head with distillation collection flask, heating mantle, thermocouple, and nitrogen inlet was charged with 97.91 g of recycled propylene glycol, 48.50 g of recycled PET polyester textile, and 0.30 g titanium tetrabutoxide (~0.1% by wt.) and heated with stirring to 200° C. for 6.0 hr. After about 5 hours, the recycled PET polyester textile had completely dissolved and appeared to be completely digested. The mixture was heated until no particles of recycled PET polyester textile remained (about 6 hr). When the digestion reaction was considered complete, the mixture was cooled to about 100° C. 65.80 g of Soybean Oil and 37.50 g of Phthalic Anhydride were added, while the mixing rate was increased to 200 rpm. When the addition was complete the mixture was then heated to 210° C. Water generated in the condensation reaction was collected in the distillation flask until roughly the theoretical amount was removed. When the reaction was complete, the digested intermediate was allowed to cool to 100° C. and then decanted from the reactor. Any large residual solids were removed by filtration through cheesecloth. The resulting opaque dark purple-red polyol had an OHV (hydroxyl value) of 420.7 mg KOH/g of sample and a viscosity at 25° C. of 576 cP (centipoise). The final product was then further filtered through a Buchner funnel with filter paper to remove any residual solids that were not removed by the cheesecloth. The resulting filtered transparent dark purple-red polyol had an OHV (hydroxyl value) of 430.0 mg KOH/g of sample and a viscosity at 25° C. of 588 cP (centipoise). See Acid Source Example 4 (unfiltered) and Example 5 (filtered) in Table 1.

Example V: Preparation of Digested Intermediate from Tritan Copolyester

A 1000 mL reactor equipped with an overhead mixer, Vigreux column, short path condenser head with distillation collection flask, heating mantle, thermocouple, and nitrogen inlet was charged with bio-based 1,3-Propanediol (40.50% by weight), Tritan Copolyester flake commercially available from Eastman (combination of dimethyl terephthalate, 1,4-cyclohexanedimethanol, and 2,2,4,4-tetramethyl-1,3-cyclobutanediol, see https://pubs.acs.org/cen/coverstory/89/8923cover4.html) (20.00% by weight), and titanium tetrabutoxide (~0.1% by weight). The mixture was heated to 205° C. with a stirring rate of 220 rpm and nitrogen flow of ~0.5 SCFH for 6 hours. After about 4 hours, the Tritan Copolyester flake had completely dissolved and appeared to be completely digested. The mixture was heated until no particles of Tritan Copolyester flake remained (about 5 hr). The mixture was cooled to about 100° C. Bio-based succinic acid (39.40% by weight) was added, while the mixing rate was increased to 350 rpm. When the addition was complete, the mixture was then heated to 205° C., and the nitrogen flow rate was increased to ~1.0 SCFH (standard cubic feet per hour). Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. The resulting opaque grey polyol had an OHV (hydroxyl value) of 239 mg KOH/g of sample and a viscosity at 25° C. of 5,800 cP (centipoise). See Acid Source Example 8 in Table 1.

Example VI: Preparation of Digested Intermediate from Polymer of Cyclohexanedimethanol Terephthalic Acid (PCTA)-1

A 1000 mL reactor equipped with an overhead mixer, Vigreux column, short path condenser head with distillation collection flask, heating mantle, thermocouple, and nitrogen inlet was charged with recycled propylene glycol (9.70% by weight), bio-based glycerol (1.75% by weight), neopentyl glycol (16.39% by weight), recycled PCTA flake commercially available from Eastman (38.80% by weight), and monobutyltin tin hydroxide (~0.15% by weight). The mixture was heated to 200° C. with a stirring rate of 150 rpm and nitrogen flow of ~0.5 SCFH for 4 hours. After about 3 hours, the recycled PCTA flake had completely dissolved and appeared to be completely digested. The mixture was heated until no particles of recycled PCTA flake remained (about 4 hr). The mixture was cooled to about 100° C. Bio-based succinic acid (39.40% by weight) and isopthalic acid (8.68% by weight) were added, while the mixing rate was increased to 350 rpm. When the addition was complete, the mixture was then heated to 200° C., and the nitrogen flow rate was increased to ~1.0 SCFH. Water generated in the condensation reaction was collected in the distillation flask until roughly the theoretical amount was removed. When the reaction was complete as determined by a low acid value (less than 5 mgKOH/g), the digested intermediate was cut with n-Butyl acetate (targeted 80% solids). The intermediate polyol and solvent was mixed for around 1.5 hrs at 120° C. and was allowed to cool to 100° C. and then decanted from the reactor. Any large residual solids were removed by filtration through cheesecloth. The resulting translucent grey polyol had an OHV (hydroxyl value) of 36 mg KOH/g of sample and a viscosity at 50° C. of 24,000 cP (centipoise) at a dilution of 81.57% by weight solids in n-Butyl acetate. See Acid Source Example 9 in Table 1.

Example VII: Preparation of Digested Intermediate from Polymer of Cyclohexanedimethanol Terephthalic Acid (PCTA)-2

A 500 mL reactor equipped with an overhead mixer, Vigreux column, short path condenser head with distillation collection flask, heating mantle, thermocouple, and nitrogen inlet was charged with Cyclohexanedimethanol (50.00% by weight), recycled PCTA flake commercially available from Eastman (30.00% by weight), and titanium tetrabutoxide (~0.1% by weight). The mixture was heated to 200° C. with a stirring rate of 150 rpm and nitrogen flow of ~0.5 SCFH for 3 hours. After about 2 hours, the recycled PCTA flake had completely dissolved and appeared to be completely digested. The mixture was heated until no particles of recycled PCTA flake remained (about 3 hr). The mixture was cooled to about 100° C. Dimer fatty acid Priol 1017 (10.00% by weight) commercially available from Croda and terephthalic acid (10.00% by weight) were added, while the mixing rate was increased to 350 rpm. When the addition was complete, the mixture was then heated to 205° C., and the nitrogen flow rate was increased to ~1.0 SCFH. Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. The resulting opaque grey polyol had an OHV (hydroxyl value) of 321.7 mg KOH/g of sample. See Acid Source Example 10 in Table 1.

Example VIII: Digestion of Recycled Polyurethane Foam

A 500 mL reactor equipped with an overhead mixer, condenser, heating mantle, thermocouple, and nitrogen inlet is charged with 232.14 g of the digested intermediate product described above from Example I and 30.41 g of recycled flexible polyurethane foam (Carex Health Brands knee pillow memory foam). The foam was cut to form pieces approximately 0.5 inches in diameter prior to introduction in the reactor. Stirring with heating and nitrogen purge was initiated until a temperature of 150° C. was achieved. After approximately 2 hours, the foam had completely dissolved. The temperature was raised to 180° C. for another 30 minutes and then heating was turned off. The mixture was poured out of the reactor at a temperature of 100° C. The resulting polyester polyol had an OHV of 321 mg KOH/g of sample, a viscosity of 8098 cP at 25° C. Upon storing the polyol for several days, no settling was observed in the dark green, opaque, but flowable product.

The 4,4'-methylenedianiline (MDA) content of this polyol was determined to be 4405 ppm initially by gas chromatography. A small sample of the polyol was heated to 100° C., and treated with an equimolar (based on MDA content) amount of Cardura™ E10P with stirring for about 2 hours. Cardura E10P is the glycidyl ester of a synthetic saturated monocarboxylic acid of highly branched C10 isomers. The resulting MDA content was reduced to 2075 ppm as measured by gas chromatography, indicating that the MDA content in these recycled PU foam polyols can be reduced by the utilization of amine scavengers, though optimization of the conditions and perhaps the type of scavenger appear to warrant further study.

Example IX: Digestion of Goose Down

A 500 mL reactor equipped with an overhead mixer, condenser, heating mantle, thermocouple, and nitrogen inlet is charged with 144.1 g of rPET, 159.9 g of recycled propylene glycol, 0.5 g of titanium tetrabutoxide (0.1% by wt.), and 28.28 g of goose down feathers. The temperature was raised to 186° C. with stirring. Reflux was observed and the temperature was raised to 200° C. A Dean Stark trap was added to collect the refluxing liquid. After about 3 hours, the goose down had completely dissolved, and the reaction was cooled to 100° C., whereupon the contents of the Dean Stark trap were added back into the reaction mixture and stirred to homogenize the mixture. One half of the reactor contents (104.72 g) were poured into a bottle to permit hydrophobe modification of the second half. This dark brown polyester polyol (Polyol Example 22 in Table 2) yielded an acid value of 2.1 mg KOH/g, an OHV of 664.1, a viscosity of 2946 cP at 25° C. and no settling after several days.

Dimer fatty acid (135.12 g, 0.345 mole) was added to the remaining polyester polyol product and the temperature raised to 185° C. for 4 hours, followed by further heating at between 180 and 200° C. for another 10 hours. The resulting dark brown polyester polyol (Polyol Example 23 in Table 2) yielded an acid value of 2.8 mg KOH/g and an OHV of 336.4 g KOH/g, a viscosity of 7113 cP at 25° C. and had no settling over the course of several days.

Example X: Digestion of Poly(Bisphenol A Carbonate)

A 500 mL reactor equipped with an overhead mixer, condenser, heating mantle, thermocouple, and nitrogen inlet was charged with 28.55 g of poly(bisphenol A carbonate) and 198.22 g of Stepanpol™ PS-2352 (available from Stepan Company) and heated with stirring to 200° C. for 5.5 hr. After about 3 hours, the poly(bisphenol A carbonate) had completely dissolved and appeared to be completely digested. The resulting pale orange, transparent polyester polyol (Polyol Example 38 in Table 2) yielded an acid value of 7.4 mg KOH/g, an OHV of 220.0, a viscosity of 15207 cps at 25° C. and no settling after several days.

Example XI: Digestion of Potato Starch

A 500 mL reactor equipped with an overhead mixer, condenser, heating mantle, thermocouple, and nitrogen inlet is charged with 96.0 g of rPET, 114.33 g of recycled propylene glycol, 0.25 g of titanium tetrabutoxide (0.1% by wt.), and 25.5 g of potato starch. The temperature was raised to 185° C. for 2 hours with stirring. Reflux was observed and the temperature was raised to 195° C. for another 3 hours. At this point the heat was turned off for the day, and the digestion, based on amount of dissolved potato starch was approximately 85% complete. The next day, the heat was turned back on for another 2 hours to a temperature of 196° C. Although the reaction product was very dark brown, there was no evidence of undissolved potato starch. The reaction was cooled to 105° C. and p-toluene sulfonic acid (0.26 g) was added followed by raising the temperature to 150° C. for one hour. A Dean Stark trap was added to collect refluxing liquid. The reaction mixture was then heated to 200° C. for about 30 minutes. At this point, only 0.22 mL of water were collected, and the reaction mixture was quite dark. The reaction mixture was then cooled to 50° C. and diethanol amine (0.20 g) added. The product was allowed to stir at this temperature for another 30 minutes and then allowed to cool to room temperature. This dark brown polyester polyol (Polyol Example 34 in Table 2) yielded an acid value of 6.4 mg KOH/g, an OHV of 396.7, a viscosity of 5632 cP at 25° C. and no apparent settling after several days.

Example XII: Digestion of Goose Down

A 1 L reactor equipped with an overhead mixer, condenser, heating mantle, thermocouple, and nitrogen inlet is charged with 351.1 g of diethylene glycol, followed by eleven additions of goose down at a reaction temperature of 180-185° C., each averaging 26.04 g over the course of the next 23 hours. Prior to each addition, the reaction mixture was inspected visually prior to adding another aliquot of goose down to insure that the previous addition had undergone full digestion and dissolution.

At this point, the polyester polyol was cooled to 121° C. and 299.3 g of the product were removed from the reactor. This dark brown polyester polyol (Polyol Example 24 in Table 1) yielded an acid value of 25.7 mg KOH/g, an OHV of 622.1, a viscosity of 3488 cP at 25° C. and no apparent settling after several days at room temperature. A similar procedure was used for (Polyol Example 27 in Table 2), except that the goose down was added together with the diethylene glycol in a single addition, followed by stirring at between 180 and 200° C.

A Dean Stark trap was connected to the reactor and ricinoleic acid (40% by wt. based on the remaining polyester polyol remaining in the reactor) was added. The contents were heated with stirring to 185° C. for 2.6 hours. This dark brown polyester polyol (Polyol Example 25 in Table 2) yielded an acid value of 14.0 mg KOH/g, an OHV of 369.9, a viscosity of 980.2 cP at 25° C. and no apparent settling after several days at room temperature.

Example XIII: Digestion of Nylon-6,6 Carpet

A 500 mL reactor equipped with an overhead mixer, virgeux column, short path condenser head with distillation collection flask, heating mantle, thermocouple, and nitrogen inlet was charged with 76.21 g of recycled propylene glycol, 50.19 g of recycled nylon-6,6 carpet, and 0.30 g titanium tetrabutoxide (~0.1% by wt.) and heated with stirring to 200° C. for 1.0 hr. After about 1 hour, it did not appear that the recycled nylon-6,6 carpet was digesting, the mixture was cooled to 100° C. and 72.00 g of recycled diethylene glycol was added. The mixture was heated again to 200° C. until no particles of recycled nylon-6,6 carpet remained (about 6 hr). After about 6.0 hours, the recycled nylon-6,6 carpet had completely dissolved and appeared to be completely digested. When the digestion reaction was considered complete, the mixture was cooled to about 100° C. 132.00 g of soybean oil and 72.13 g of phthalic anhydride were added, while the mixing rate was increased to 200 rpm. When the addition was complete the mixture was then heated to 210° C. Water generated in the condensation reaction was collected in the distillation flask until roughly the theoretical amount was removed. When the reaction was complete, the digested intermediate was allowed to cool to 100° C. and then decanted from the reactor. The resulting polyol consisted of two non-digestible phases and one polyol phase. The two non-digestible phases was a grey solid chuck of polyolefin and latex adhesives, as well as grey calcium carbonate particulate residue that settled at the bottom. Any large residual solids (polyolefin and latex adhesive chuck) were removed by filtration through cheesecloth. The final product was then further filtered through a Buchner funnel with a filter paper to remove any residual solids that were not removed by the cheesecloth (calcium carbonate particulate). The resulting filtered opaque brown polyol had an OHV (hydroxyl value) of 353.7 mg KOH/g of sample and a viscosity at 25° C. of 601 cP (centipoise). See Polyol Example 40 in Table 2.

Example XIV: Digestion of Chicken Feather Meal

A 500 mL reactor equipped with an overhead mixer, Vigreux column, short path condenser head with distillation collection flask, heating mantle, thermocouple, and nitrogen inlet was charged with 101.46 g of recycled diethylene glycol, 27.95 g of chicken feather meal, and 0.30 g titanium tetrabutoxide (~0.1% by wt.) and heated with stirring to 210° C. for 3 hr. After about 2 hours, the chicken feather meal had completely dissolved and appeared to be completely digested. The mixture was heated until no particles of chicken feather meal remained (about 2.5 hr). When the digestion reaction was considered complete, the mixture was cooled to about 100° C. 98.00 g of soybean oil and 25.00 g of phthalic anhydride were added, while the mixing rate was increased to 200 rpm. When the addition was complete the mixture was then heated to 215° C. Water generated in the condensation reaction was collected in the distillation flask until roughly the theoretical amount was removed. When the reaction was complete, the digested intermediate was allowed to cool to 100° C. and then decanted from the reactor. Any residual particles were removed by filtration through cheesecloth. The resulting opaque dark black-brown polyol had an OHV (hydroxyl value) of 351.6 mg KOH/g of sample and a viscosity at 25° C. of 196.5 cP (centipoise).

Example XV: Digestion of Corn Zein

A 5000 mL reactor equipped with an overhead mixer, Vigreux column, short path condenser head with distillation collection flask, heating mantle, thermocouple, and nitrogen inlet was charged with 1447.17 g of recycled diethylene glycol and 298.50 g of corn zein and heated with stirring to 40° C. for 2 hr. After about 2 hours, the corn zein had completely dissolved in the recycled diethylene glycol. When the corn zein had completely dissolved in the recycled diethylene glycol, the mixture was heated to about 100° C. 1023.00 g of phthalic anhydride and 1.40 g titanium tetrabutoxide (~0.1% by wt.) were added, while the mixing rate was increased to 200 rpm. When the addition was complete the mixture was then heated to 200° C. After about 2 hours, the mixture was heated to about 210° C. Water generated in the condensation reaction was collected in the distillation flask until roughly the theoretical amount was removed. Throughout the duration of the reaction, aliquots of the digestion were taken to check hydroxyl and acid values. Low acid numbers can be ensured by driving the condensation step (with digestible polymer) to the desired level of completion or by adding an acid scavenger (e.g., Cardura™ E10P glycidyl ester manufactured by Momentive) at the conclusion of the condensation step. As suggested above, it is acceptable practice to adjust acid numbers if necessary for a particular application with an acid scavenger such as, for example, an epoxide derivative, and this treatment can be performed by the manufacturer, distributor, or end user. 40.00 g of Cardura™ E10P glycidyl ester acid scavenger was added to ensure a low acid value. In order to stay in a target hydroxyl value range, the addition of recycled diethylene glycol is necessary. After about 12 hours, the mixture was cooled to about 100° C. 300.00 g of recycled diethylene glycol was added, while the mixing rate was increased to 200 rpm. When the addition was complete the mixture was then heated to 200° C. When the reaction was complete as determined by a low acid value (less than 5), the digested intermediate was allowed to cool to 100° C. and then decanted from the reactor. Any residual particulates were removed by filtration through cheesecloth. The resulting opaque dark black-brown polyol had an OHV (hydroxyl value) of 265.0 mg KOH/g of sample and a viscosity at 25° C. of 4045 cP (centipoise).

Example XVI: Digestion of Soy Flour

A 500 mL reactor equipped with an overhead mixer, Vigreux column, short path condenser head with distillation collection flask, heating mantle, thermocouple, and nitrogen inlet was charged with 87.50 g of recycled propylene glycol, 62.53 g of recycled polyethylene terephthalate pellets, 25.04 g of Soy flour, and 0.30 g titanium tetrabutoxide (~0.1% by wt.) and heated with stirring to 205° C. for 1.0 hr. After about 5 hours, the soy flour and recycled polyethylene terephthalate pellets had completely dissolved and appeared to be completely digested. The mixture was heated until no particles of soy flour and recycled polyethylene terephthalate pellets remained (6 hr). When the digestion reaction was considered complete, the mixture was cooled to about 100° C. 71.90 g of soybean oil was added, while the mixing rate was increased to 200 rpm. When the addition was complete the mixture was then heated to 210° C. Water generated in the condensation reaction was collected in the distillation flask until roughly the theoretical amount was removed. When the reaction was complete, the digested intermediate was allowed to cool to 100° C. and then decanted from the reactor. Any residual particulates were removed by filtration through cheesecloth. The resulting opaque dark black-brown polyol had an OHV (hydroxyl value) of 384.9 mg KOH/g of sample and a viscosity at 25° C. of 872.1 cP (centipoise).

Example XVII: Digestion of Polysaccharide (Pectin)

A 500 mL reactor equipped with an overhead mixer, Vigreux column, short path condenser head with distillation collection flask, heating mantle, thermocouple, and nitrogen inlet was charged with the digested intermediate product (76.5% by weight) as described above from Example I and pectin (23.5% by weight). The mixture was heated to 210° C. with a stirring rate of 150 rpm and nitrogen flow of ~0.5 SCFH for 12 hours. Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. Undigested pectin was removed by filtration through a glass fritted disc filter size 'F' (<5 μm) at about 80° C. The resulting transparent dark brown polyol had an OHV (hydroxyl value) of 228.3 mg KOH/g of sample and a viscosity at 25° C. of 5,733 cP (centipoise). See, Polyol Example 41 in Table 2.

Example XVIII: Digestion of Recycled Poly(Bisphenol a Carbonate)-1

A 500 mL reactor equipped with an overhead mixer, Vigreux column, short path condenser head with distillation collection flask, heating mantle, thermocouple, and nitrogen inlet was charged with recycled propylene glycol (17% by weight), recycled polyethylene terephthalate pellets (39% by weight), recycled poly(bisphenol A carbonate) pellets (9% by weight), bio-based BiOH® 5300 polyol (17% by weight) commercially available from Cargill, and titanium tetrabutoxide (~0.1% by weight). The mixture was heated to 200° C. with a stirring rate of 150 rpm and nitrogen flow of ~0.5 SCFH for 6 hours. After about 5 hours, the recycled polyethylene terephthalate and recycled poly(bisphenol A carbonate) pellets had completely dissolved and appeared to be completely digested. The mixture was heated until no particles of recycled polyethylene terephthalate and recycled poly(bisphenol A carbonate) pellets remained (about 6 hr). The mixture was cooled to about 100° C. Bio-based succinic acid (17.9% by weight) was added, while the mixing rate was increased to 350 rpm. When the addition was complete, the mixture was then heated to 205° C., and the nitrogen flow rate was increased to ~1.0 SCFH. Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. The resulting translucent dark amber polyol had an OHV (hydroxyl value) of 134.1 mg KOH/g of sample and a viscosity at 100° C. of 9,000 cP (centipoise). See, Polyol Example 42 in Table 2.

Example XIX: Digestion of Recycled Poly(Bisphenol A Carbonate)-2

A 500 mL reactor equipped with an overhead mixer, Vigreux column, short path condenser head with distillation collection flask, heating mantle, thermocouple, and nitrogen inlet was charged with Stepanpol PN 110 (85% by weight) a neopentyl glycol-phthalic anhydride-based polyester polyol commercially available from the Stepan Company, and recycled poly(bisphenol A carbonate) pellets (15% by weight). The mixture was heated to 210° C. with a stirring rate of ~50 rpm and nitrogen flow of ~0.8 SCFH for 1 hour. After about 1 hour, the recycled poly(bisphenol A carbonate)

pellets had completely dissolved and appeared to be completely digested. The mixture stirring rate was then increased to ~150 rpm for 3 hours. The mixture was heated until no particles of recycled poly(bisphenol A carbonate) pellets remained (about 4 hr). Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. The resulting opaque white polyol had an OHV (hydroxyl value) of 73.6 mg KOH/g of sample and a viscosity at 75° C. of 9,410 cP (centipoise). See, Polyol Example 43 in Table 2.

Example XX: Digestion of Recycled Poly(Bisphenol A Carbonate)-3

Part A. Preparation of digested intermediate from recycled polyethylene terephthalate pellets: A 500 mL reactor equipped with an overhead mixer, Vigreux column, short path condenser head with distillation collection flask, heating mantle, thermocouple, and nitrogen inlet was charged with recycled propylene glycol (15.48% by weight), recycled polyethylene terephthalate pellets (49.95% by weight), trimethylolpropane (5.49% by weight), and butyltin hydroxide oxide hydrate (~0.1% by weight). The mixture was heated to 200° C. with a stirring rate of 150 rpm and nitrogen flow of ~0.5 SCFH for 7 hours. After about 5 hours, the recycled polyethylene terephthalate pellets had completely dissolved and appeared to be completely digested. The mixture was heated until no particles of recycled polyethylene terephthalate pellets remained. The mixture was cooled to about 100° C. Bio-based succinic acid (17.9% by weight) and dimer fatty acid Priol 1017 (14.24% by weight) commercially available from Croda was added, while the mixing rate was increased to 350 rpm. When the addition was complete, the mixture was then heated to 200° C. with a stirring rate of 150 rpm and the nitrogen flow was increased to ~1.0 SCFH. Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. The resulting transparent dark amber polyol had an OHV (hydroxyl value) of 103.7 mg KOH/g of sample and a viscosity at 100° C. of 6,035 cP (centipoise).

Part B: Digestion or recycled poly(bisphenol A carbonate): A 500 mL reactor equipped with an overhead mixer, Vigreux column, short path condenser head with distillation collection flask, heating mantle, thermocouple, and nitrogen inlet was charged with a previously prepared aromatic polyester polyol (see Part A, above) (65% by weight) and recycled poly(bisphenol A carbonate) pellets (8% by weight). The mixture was heated to 210° C. with a stirring rate of ~50 rpm and nitrogen flow of ~0.8 SCFH for 1 hour. After about 1 hour, the recycled poly(bisphenol A carbonate) pellets had completely dissolved and appeared to be completely digested. The mixture stirring rate was then increased to ~150 rpm for 3 hours. The mixture was heated until no particles of recycled poly(bisphenol A carbonate) pellets remained (about 4 hr). Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. The resulting translucent green polyol had an OHV (hydroxyl value) of 93.6 mg KOH/g of sample and a viscosity at 25° C. of 31,056 cP (centipoise), note that the polyol was cut with xylene to around 79% solids to achieve this viscosity reading. See, Polyol Example 44 in Table 2.

Example XXI: Digestion of Recycled Poly(Bisphenol A Carbonate)-4

A 500 mL reactor equipped with an overhead mixer, Vigreux column, short path condenser head with distillation collection flask, heating mantle, thermocouple, and nitrogen inlet was charged with a previously prepared aromatic polyester polyol [see digestion of recycled poly(bisphenol A carbonate)—BP1000P-2.6A as described in the above Example XV] (65% by weight) and bio-based glycerol (5% by weight). The mixture was heated to 210° C. with a stirring rate of ~150 rpm and nitrogen flow of ~0.8 SCFH for 2 hours. The mixture was then cooled to about 100° C. and bio-based linoleic Acid (30% by weight) was added, while the mixing rate was increased to 350 rpm. When the addition was complete, the mixture was then heated to 210° C., and nitrogen was increased to ~1.0 SCFH. Water generated in the condensation reaction was collected in the distillation flask until roughly the theoretical amount was removed. When the reaction was complete as determined by a low acid value (less than 5 mgKOH/g), the digested intermediate was allowed to cool to 100° C. Recycled poly(bisphenol A carbonate) pellets (3.25% by weight) was then added while the mixing rate was increased to 350 rpm. When the addition was complete the mixture was heated to 210° C. until no particles of recycled poly(bisphenol A carbonate) pellets remained (about 4 hr). The digested intermediate was allowed to cool to 100° C. and then decanted from the reactor. Any large residual solids were removed by filtration through cheesecloth. The resulting transparent golden polyol had an OHV (hydroxyl value) of 91.2 mg KOH/g of sample and a viscosity at 50° C. of 5,768 cP (centipoise). See, Polyol Example 45 in Table 2.

Example XXII: Digestion of Recycled Poly(Bisphenol A Carbonate)-5

A 1000 mL reactor equipped with an overhead mixer, Vigreux column, short path condenser head with distillation collection flask, heating mantle, thermocouple, and nitrogen inlet was charged with recycled propylene glycol (7.8% by weight), recycled polyethylene terephthalate pellets (31.2% by weight), recycled poly(bisphenol A carbonate) pellets (19.5% by weight), bio-based glycerol (1.4% by weight), neopentyl glycol (13.2% by weight), and butyltin hydroxide oxide hydrate (~0.1% by weight). The mixture was heated to 200° C. with a stirring rate of 300 rpm and nitrogen flow of ~0.3 SCFH for 6 hours. After about 5 hours, the recycled polyethylene terephthalate and recycled poly(bisphenol A carbonate) pellets had completely dissolved and appeared to be completely digested. The mixture was heated until no particles of recycled polyethylene terephthalate and recycled poly(bisphenol A carbonate) pellets remained (about 6 hr). When the digestion reaction was considered complete, the mixture was cooled to about 100° C. Bio-based succinic acid (19.8% by weight) and isophthalic acid (7% by weight) were added, while the mixing rate was increased to 300 rpm.

When the addition was complete, the mixture was then heated to 205° C., and nitrogen was increased to ~1.0 SCFH. Water generated in the condensation reaction was collected in the distillation flask until roughly the theoretical amount was removed. When the reaction was complete as determined by a low acid value (less than 5 mgKOH/g), the digested intermediate was allowed to cool to 100° C. and then decanted from the reactor. Any large residual solids were removed by filtration through cheesecloth. The resulting translucent green polyol had an OHV (hydroxyl value) of 75.3 mg KOH/g of sample. See, Polyol Example 46 in Table 2.

Example XXIII: Digestion of Recycled Poly(Bisphenol A Carbonate)-6

A 500 mL reactor equipped with an overhead mixer, Vigreux column, short path condenser head with distillation collection flask, heating mantle, thermocouple, and nitrogen inlet was charged with a previously prepared aromatic polyester polyol [Preparation of Digested Intermediate from Tritan Copolyester as described in the above Example V] (90.63% by weight) and recycled Poly(Bisphenol a carbonate) pellets (9.37% by weight). The mixture was heated to 205° C. with a stirring rate of ~150 rpm and nitrogen flow of ~0.8 SCFH for 4 hours. After about 2 hours, the recycled Poly(Bisphenol a carbonate) pellets had completely dissolved and appeared to be completely digested. The mixture was heated until no particles of recycled Poly(Bisphenol a carbonate) pellets remained (about 4 hr). The digested intermediate was allowed to cool to 100° C. and then decanted from the reactor. Any large residual solids were removed by filtration through cheesecloth. The resulting transparent yellow-gold polyol had an OHV (hydroxyl value) of 202.1 mg KOH/g of sample and a viscosity at 25° C. of 17,496 cP (centipoise). See, Polyol Example 47 in Table 2.

Example XXIV: Digestion of Recycled Poly(Bisphenol A Carbonate)-7

A 500 mL reactor equipped with an overhead mixer, Vigreux column, short path condenser head with distillation collection flask, heating mantle, thermocouple, and nitrogen inlet was charged with a previously prepared aromatic polyester polyol [Preparation of Digested Intermediate from PCTA as described in the above Example VI] (90.53% by weight) and recycled Poly(Bisphenol a carbonate) pellets (9.47% by weight). The mixture was heated to 205° C. with a stirring rate of ~150 rpm and nitrogen flow of ~0.8 SCFH for 4 hours. After about 2 hours, the recycled Poly(Bisphenol a carbonate) pellets had completely dissolved and appeared to be completely digested. The mixture was heated until no particles of recycled Poly(Bisphenol a carbonate) pellets remained (about 4 hr) and then was cut with n-Butyl acetate (targeted 60% solids). The intermediate polyol and solvent was mixed for around 0.5 hrs at 120° C. and was allowed to cool to 100° C. and then decanted from the reactor. Any large residual solids were removed by filtration through cheesecloth. The resulting opaque green polyol had an OHV (hydroxyl value) of 36.4 KOH/g of sample. See, Polyol Example 48 in Table 2.

Example XXV: Digestion of Recycled Poly(Bisphenol A Carbonate)-8

A 500 mL reactor equipped with an overhead mixer, Vigreux column, short path condenser head with distillation collection flask, heating mantle, thermocouple, and nitrogen inlet was charged with a previously prepared aromatic polyester polyol [Preparation of Digested Intermediate from PCTA as described in the above Example VII] (90.96% by weight) and recycled Poly(Bisphenol a carbonate) pellets (9.04% by weight). The mixture was heated to 205° C. with a stirring rate of ~150 rpm and nitrogen flow of ~0.8 SCFH for 4 hours. After about 2 hours, the recycled Poly(Bisphenol a carbonate) pellets had completely dissolved and appeared to be completely digested. The mixture was heated until no particles of recycled Poly(Bisphenol a carbonate) pellets remained (about 4 hr). The digested intermediate was allowed to cool to 100° C. and then decanted from the reactor. Any large residual solids were removed by filtration through cheesecloth. The opaque, light grey polyol had an OHV (hydroxyl value) of 255.0 KOH/g of sample. See, Polyol Example 49 in Table 2.

Example XXVI: Procedure for Preparing Polyurethane Coatings

The following is a procedure for making a two-component ("2 K") coating. The polyester polyol (14.11 g, 0.098 equiv.), 2-methyl-1,3-propanediol (0.7 g, 0.008 equiv.), and ethylene glycol (1.12 g, 0.037 equiv.) were added to an 250 mL beaker, at room temperature. Hexamethylene diisocyanate (8.97 g, 0.107 equiv.) and isophorone diisocyanate (5.08 g, 0.023 equiv.) were then added to the beaker. The mixture was then diluted to 50% by weight with 2-butanone. Mechanical mixing was initiated using a tri-lobe agitation blade measuring 3 inches in diameter and mixing was gradually increased until 500 RPM was reached and a homogeneous mixture resulted. Dibutyltin dilaurate (0.05% by wt.) was then added to the reaction mixture. After approximately 5 minutes of reaction time and ensuing 10° C. exotherm, a bead of the reacting mixture was applied to one side of each of five aluminum panels measuring 4 in. by 6 in. The beads of solvent-borne polyurethane were then drawn down each panel into a wet film using a #50 R.D. Specialties drawdown bar to a wet film thickness of 4.5 mils. The panels were allowed to flash dry in a hood at ambient temperatures for at least one hour, and then heated to 110° C. for 1.5-2 hours to permit complete conversion to polyurethane.

The final dry film thickness was determined using a PosiTector 6000 (Defelsko Corporation) dry film thickness gage. Konig hardness was measured using ISO 1522 using a TQC Pendulum Hardness Tester (Model SPO500). Pencil scratch hardness was measured using ASTM D3363. Flexibility was measured using ASTM D522. Adhesion was measured using ASTM D3359. Stain testing was measured using ASTM D1308. MEK double rub testing was conducted using ASTM D4752. Table 3 summarizes testing data on these polyurethane coatings.

Example XXVII: Procedure for Preparing Powder Coatings

The following is a procedure for making a powder coating. A 500 mL reactor equipped with an overhead mixer, condenser, heating mantle, thermocouple, and nitrogen inlet is charged with 67.50 g of poly(bisphenol A carbonate), 180 g recycled PET pellet, 67.50 g diethylene glycol, 46.04 g glycerol, and 0.10 g monobutyltin oxide catalyst and heated with stirring to 200° C. for 8 hours, or until the PET pellets are solubilized. The temperature is then reduced to 100° C. and 142.32 g isophthalic acid is added and the temperature is then set to 175° C. After 1.5 hours the temperature is increased to 185° C., where it is held for 30 min. The temperature is then increased to 195° C., where it is held for 2 hours. The temperature is further increased to 205° C. The reaction is continued to run for a total of 25-26 hours, or until the acid value is about 5.5 mg KOH/g. The resultant polyester polyol is poured out and allowed to cool, dried and ground a powder. Next 500 g of the ground polyester polyol powder, 300 g titanium dioxide pigment (R-902+ from DuPont), 438 g caprolactam blocked isocyanurate, 6.1 g BYK 366P flow agent (an acrylic surface active agent), 3.5 g benzoin, and 2 g K-Kat 348 bismuth carboxylate catalyst (King Industries), are blended in a GlenMills Turbula dyna-MIX blender, and then extruded through a laboratory scale twin screw extruder with zone temperatures of 35 and 95° C. The extrudate is cooled, ground, and sieved to provide a fine powder coating having a size of less than 105 microns. This powder coating is useful for application to a metal substrate using electrostatic or fluidized bed technology.

Example XXVIII: Procedure for Making Rigid Polyisocyanurate Foams

The following is a procedure for making a rigid polyisocyanurate foam. The polyester polyol is formulated by weighing the components of the polyol side of the ingredients (B-side) into a plastic beaker, followed by a 30 second mix using a 4 inch wide Cowles mixing blade. The components of the B-side include the polyester polyol, water, surfactant, flame retardant, blowing agent and catalysts. The isocyanate side of the ingredients (A-side), includes Papi 27, which is a polymethylene polyphenyl isocyanate that contains MDI (4,4'-methylene diphenyl diisocyante), which is available from the Dow Chemical Co. An isocyanate/OH equivalent ratio of 2.6/1.0 is used to prepare the polyisocyanurate foams by weighing the A-side and adding it quickly to the B-side followed by mixing for 4 seconds at 3000 rpm using a drill press equipped with a 4 inch Cowles mix blade. The foaming mixture is poured into a 12"×12"×12" cardboard box, where the cream, string, rise and tack-free times are recorded. The foam is then tested using standard methodologies to determine the thermal conductivity, the density and the compressive strength. The following is a summary of the foam formulation.

Foam Formulation

| Ingredient | Target Weight | OH Number | Number of Equiv. |
|---|---|---|---|
| Polyester Polyol | 563.15 | 282 | 2.8308 |
| Fyrol PCF[1] | 64.00 | | |
| Dabco K-15[2] | 12.81 | 400 | 0.0913 |
| Polycat 5[3] | 1.01 | | 0.0000 |
| Tegostab B8465[4] | 10.10 | | 0.0000 |
| Water | 2.53 | 6233 | 0.2806 |
| n-Pentane | 146.41 | | 0.0000 |
| totals | 800.00 | | 3.2027 |
| Resin eq. wt. | 250 | Resin OHV = | 224.6 |
| Iso eq. wt. | 134 | | |
| Wt. Ratio (A/B) | 1.3948 | | |
| Parts by Wt. A | 58.2 | | |
| Parts by Wt. B | 41.8 | | |
| NCO/OH index | 260.00 | | |

[1]Tris(2-chloroisopropyl)phosphate,
[2]potassium octoate in diethylene glycol,
[3]pentamethyl diethylene triamine, and
[4]silicone surfactant.

Example XXIX: Rigid Foam Made from Recycled Polyethylene Terephthalate (rPET) and Recycled Poly(Bisphenol A Carbonate) r(PBAC)

A rigid foam polyol based on rPET was prepared in a fashion described above in Example XXVIII containing 7 wt. % rPBAC. The polyol had a hydroxyl number (OHV) of 266 mg KOH/g, a viscosity of 7408, and an acid value of 4.9 mg KOH/g. Using the formulation provided in Example XXVIII combined with a 4 second mix using a 3000 rpm drill press equipped with a 4 inch Cowles mix blade, the polyol was converted into a polyisocyanurate foam. A foam cup was used to determine the cup foam density. The fine-cell foam had a compressive strength of 36 psi, a density of 1.99 lb/cu. ft. and a k-factor of 0.172 BTU*in/hr*ft$^2$*° F. (namely British Thermal Units inches per hour square foot degree Fahrenheit).

TABLE 1

Physical Characteristics of the Digestion Product from Aromatic Polyacid Sources

| Acid Source Example No. | Digestible Aromatic Polyacid Source | Wt. % Polyacid Source | Relative Amounts of Materials Used in Digestion Procedure | Catalyst |
|---|---|---|---|---|
| 1 | PET Pellets | 28.74% | 1 mole rPET/2.80 mole PG/0.46 mole Dimer Fatty Acid | 0.10% Ti(BuO)$_4$ |
| 2 | PET Carpet | 29.32% | 1 mole rPET/2.01 mole PG/0.34 mole Dimer Fatty Acid | 0.12% Ti(BuO)$_4$ |
| 3 | PTT Carpet | 30.82% | 1 mole rPTT/1.96 mole PG/0.33 mole Dimer Fatty Acid | 0.11% Ti(BuO)$_4$ |
| 4 | PET Textile (Unbacked) | 19.4% | 1 mole rPET/1.29 mole PG/0.25 mole Phthalic Anhydride/0.08 mole Soy bean oil | 0.10% Ti(BuO)$_4$ |
| 5 | PET Textile (Unbacked) -- Filtered material of example 4 | 19.4% | 1 mole rPET/1.29 mole PG/0.25 mole Phthalic Anhydride/0.08 mole Soy bean oil | 0.10% Ti(BuO)$_4$ |
| 6 | PET Textile (Backed) | 15% | 1 mole rPET/1.03 mole DEG/0.25 mole Phthalic Anhydride/0.08 mole Soy bean oil | 0.10% Ti(BuO)$_4$ |
| 7 | Polyester Fiber Fill + rPET Pellets | 34.91% | 1.32 mole rPET/2.8 mole PG/0.46 mole Dimer Fatty Acid | 0.10% Ti(BuO)$_4$ |
| 8 | Tritan Copolyester Flakes | 20.0% | 0.781 mole Tritan Copolyester/3.992 mole 1,3-Propanediol/2.502 mole Succinic Acid | 0.10% Ti(BuO)$_4$ |

TABLE 1-continued

Physical Characteristics of the Digestion Product from Aromatic Polyacid Sources

| 9 | PCTA Flake | 38.8% | 0.85 mole PTCA/0.944 mole NPG/0.765 mole PG/0.114 mole Glycerol/0.313 mole isopthalic Acid/1.247 mole Succinic Acid | 0.15% MTBO |
| 10 | PCTA Flake | 30.0% | 0.328 mole PCTA/1.04 mole CHDM/0.181 mole Terephthalic Acid/0.053 mole Dimer Fatty Acid | 0.10% Ti(BuO)$_4$ |

| Acid Source Example No. | Acid Value (mg KOH/g) | Hydroxyl Value (mg KOH/g) | Color | Settling | Clarity | Viscosity (cP) at 25° C., unless noted 50% Torque, unless noted |
|---|---|---|---|---|---|---|
| 1 | 0.9 | 380.0 | Amber | None | Transparent | 3097 |
| 2 | 0.8 | 352.0 | Dark Amber | None | Transparent | 3000 |
| 3 | 1.0 | 371.1 | Dark Amber | None | Slightly Transparent | 2307 |
| 4 | 1.1 | 420.7 | Dark Purple-Red | Slight, Before Filtration | Opaque | 576 |
| 5 | 1.3 | 430.0 | Dark Purple-Red | None | Transparent | 588 |
| 6 | 1.2 | 338.0 | Dark Purple-Red | None | Transparent | 408 |
| 7 | 0.7 | 352.0 | Yellow | Slight | Opaque | 5577 |
| 8 | 0.5 | 239.0 | Grey | Filtered | Opaque | 5800 |
| 9 | 1.2 | 36.0 | Grey | Filtered | Tranluscent | 24,000 (81.57% in n-butyal acetate) |
| 10 | 0.9 | 321.7 | Grey | Filtered | Opaque | Not flowable at 125° C. |

TABLE 2

Physical Characteristics of the Digestion Product from Digestible Polymers

| Polyol Example No. | Digestible Polymer | Wt. % Digestible Polymer | Digested Intermediate | Catalyst |
|---|---|---|---|---|
| 1 | Recycled Flexible Polyurethane Foam (Carex Health Brands Knee Pillow) | 9.44% | 1 mole rPET/3 mole PG/0.5 mole Dimer Fatty Acid | 0.5% Zn(OAc)2 present in digested intermediate |
| 2 | Recycled Polyisocyanurate Insulating Foam | 8.68% | 1 mole rPET/2.8 mole PG/0.46 mole Dimer Fatty Acid | 0.1% Ti(BuO)4 present in digested intermediate |
| 3 | Recycled Flexible Polyurethane Black Foam | 9.72% | 1 mole rPET/2.8 mole PG/0.46 mole Dimer Fatty Acid | 0.1% Ti(BuO)4 present in digested intermediate |
| 4 | Recycled Polyisocyanurate Insulating Foam | 12.62% | Polyol from Example 2 Used to digest further recycled PIR Foam | Catalyst present from Example 2 |
| 5 | Recycled Polyisocyanurate insulating foam | 4.56% | 1 mole rPET/2.8 mole PG/0.46 mole Dimer Fatty Acid | 0.1% Ti(BuO)4 present in digested intermediate |
| 6 | Goose Down Feathers | 4.37% | 1 mole rPET/2.8 mole PG/0.46 mole Dimer Fatty Acid | 0.1% Ti(BuO)4 present in digested intermediate |
| 7 | Goose Down Feathers | 4.50% | 1 mole rPET/2.8 mole PG/0.46 mole Dimer Fatty Acid | 0.1% Ti(BuO)4 present in digested intermediate |
| 8 | Poly(Bisphenol A Carbonate) | 8.80% | 1 mole rPET/2.8 mole PG/0.46 mole Dimer Fatty Acid | 0.1% Ti(BuO)4 present in digested intermediate |
| 9 | Chitin from Shrimp Shells | 7.97% | 1 mole rPET/2.8 mole PG/0.46 mole Dimer Fatty Acid | 0.1% Ti(BuO)4 present in digested intermediate |
| 10 | Cellulose | 7.93% | 1 mole rPET/2.8 mole PG/0.46 mole Dimer Fatty Acid | 0.1% Ti(BuO)4 present in digested intermediate |
| 11 | Casein from Bovine Milk | 7.89% | 1 mole rPET/2.8 mole PG/0.46 mole Dimer Fatty Acid | 0.1% Ti(BuO)4 present in digested intermediate |
| 12 | Recycled Polylactic Acid Drinking Cups | 9.18% | 1 mole rPET/2.8 mole PG/0.46 mole Dimer Fatty Acid | 0.1% Ti(BuO)4 present in digested intermediate |
| 13 | Recycled Polylactic Acid Drinking Cups | 25.83% | 1 mole rPET/2.8 mole PG/0.46 mole Dimer Fatty Acid | 0.1% Ti(BuO)4 present in digested intermediate |
| 14 | Soy Protein Acid Hydrolysate | 7.70% | 1 mole rPET/2.8 mole PG/0.46 mole Dimer Fatty Acid | 0.1% Ti(BuO)4 present in digested intermediate |
| 15 | Gluten from Wheat | 8.35% | 1 mole rPET/2.8 mole PG/0.46 mole Dimer Fatty Acid | 0.1% Ti(BuO)4 present in digested intermediate |
| 16 | Recycled Polyurethane Foam (UFP Technologies Polyether Black 30 ppi) | 10.79% | 1 mole rPET/2.8 mole PG/0.46 mole Dimer Fatty Acid | 0.1% Ti(BuO)4 present in digested intermediate |
| 17 | Nylon-6 | 5.39% | 1 mole rPET/2.8 mole PG/0.46 mole Dimer Fatty Acid | 0.1% Ti(BuO)4 present in digested intermediate |

TABLE 2-continued

Physical Characteristics of the Digestion Product from Digestible Polymers

| | | | | |
|---|---|---|---|---|
| 18 | Recycled Flexible Polyurethane Foam (Carex Health Brands Knee Pillow) | 9.44% | 1 mole rPET/2.8 mole PG/0.46 mole Dimer Fatty Acid/0.002 mole Cardura E10P | 0.1% Ti(BuO)4 present in digested intermediate |
| 19 | Chitin from shrimp shells | 9.40% | Diethylene Glycol | None |
| 20 | Goose Down Feathers | 4.67% | Diethylene Glycol | None |
| 21 | Recycled Flexible Polyurethane Foam (Carex Health Brands Knee Pillow) | 11.58% | 1 mole rPET/2.8 mole PG/0.46 mole Dimer Fatty Acid | 0.1% Ti(BuO)4 present in digested intermediate |
| 22 | Goose Down Feathers | 8.50% | 1 mole rPET/2.8 mole PG | 0.1% Ti(BuO)4 |
| 23 | Goose Down Feathers | 5.34% | 1 mole rPET/2.8 mole PG/0.46 mole (Dimer Fatty Acid added after feathers digested.) | Catalyst present from Example 22 |
| 24 | Goose Down Feathers | 44.93% | Diethylene Glycol | None |
| 25 | Goose Down Feathers | 37.07% | Diethylene Glycol/40 wt. % Ricinoleic Acid | None |
| 26 | Recycled DuPont Sorona PTT Cloth (Blue) | 9.62% | 1 mole rPET/2.8 mole PG/0.46 mole Dimer Fatty Acid | 0.1% Ti(BuO)4 present in digested intermediate |
| 27 | Goose Down Feathers | 49.55% | Diethylene Glycol | None |
| 28 | HyPep ® 4601 Protein Hydrolysate from wheat gluten | 10.57% | 1 mole rPET/2.8 mole PG/0.46 mole Dimer Fatty Acid | 0.1% Ti(BuO)4 present in digested intermediate |
| 29 | Poly(Bisphenol A Carbonate) | 25.10% | 1 mole rPET/2.8 mole PG/0.46 mole Dimer Fatty Acid | 0.1% Ti(BuO)4 present in digested intermediate |
| 30 | Zein from Corn | 10.95% | 1 mole rPET/2.8 mole PG/0.46 mole Dimer Fatty Acid | 0.1% Ti(BuO)4 present in digested intermediate |
| 31 | Soy Protein Isolate | 11.17% | 1 mole rPET/2.8 mole PG/0.46 mole Dimer Fatty Acid | 0.1% Ti(BuO)4 present in digested intermediate |
| 32 | Waste Chicken Feathers | 5.45% | 1 mole rPET/2.8 mole 3-Methyl-1,5-Pentanediol/0.3 Dimer Fatty Acid | 0.1% Ti(BuO)4 |
| 33 | Cellulose | 6.83% | 3.0 EG/1 rPET flake/1.2 Maleic Acid | 0.1% Ti(BuO)4 |
| 34 | Potato Starch | 10.02% | 1.0 mole rPET flake/3.0 mole PG/0.001 mole diethanolamine | 0.1% Ti(BuO)4/0.11% p-Toluene Sulfonic Acid |
| 35 | Chitin from Shrimp Shells | 7.44% | 1 mole rPET flake/3.0 mole EG/1.2 Maleic Acid | 0.1% Ti(BuO)4 |
| 36 | Cellulose | 7.23% | 1 mole rPET/2.8 mole PG/1.0 mole Succinic Acid | 0.1% Ti(BuO)4 |
| 37 | Cellulose | 7.05% | 1 mole rPET flake/3 mole PG/1.1 Maleic Acid | 0.1% Ti(BuO)4 |
| 38 | Poly(Bisphenol A Carbonate) | 12.59% | 87.41% Stepanol 2352 (Contains Phthalic Anhydride and Diethylene Glycol) | Unknown |
| 39 | Nylon-6,12 | 9.25% | 1 mole rPET/2.8 mole PG/0.46 mole Dimer Fatty Acid | 0.1% Ti(BuO)4 present in digested intermediate |
| 40 | Nylon-6,6 Carpet | 12.5% | 0.68 mole DEG/1.00 mole PG/0.49 mole Phthalic Anhydride/0.15 mole Soy bean oil | 0.1% Ti(BuO)4 |
| 41 | Pectin | 23.5% | 1 mole rPET/2.8 mole PG/0.36 mole Dimer Fatty Acid | 0.1% Ti(BuO)4 |
| 42 | Recycled Poly(Bisphenol A Carbonate) (Example XVIII) | 9.0% | 1 mole rPET/1.10 mole PG/0.06 mole Cargill BiOH 5300 (Vegetable Oil based)/0.75 mole Succinic Acid | 0.1% Ti(BuO)4 |
| 43 | Recycled Poly(Bisphenol A Carbonate) (Example XIX) | 15.0% | 85 wt % Stepanpol PN 110 (neopentyl glycol-phthalic anhydride-based polyester polyol) | NA |
| 44 | Recycled Poly(Bisphenol A Carbonate) (Example XX) | 8.0% | 1 mole rPET/0.78 mole PG/0.16 mole Trimethylolpropane/0.48 mole Succinic Acid/0.10 mole Dimer Fatty Acid | 0.1% MTBO (Butyltin hydroxide oxide hydrate) |
| 45 | Recycled Poly(Bisphenol A Carbonate) (Example XXI) | 9.0% | 65 wt % Polyol Example 42/30 wt % Linoleic Acid/5 wt % Glycerol | 0.1% Ti(BuO)4 present in digested intermediate |
| 46 | Recycled Poly(Bisphenol A Carbonate) (Example XXII) | 19.5% | 1 mole rPET/0.78 mole Neopentyl Glycol/0.63 mole PG/0.1 mole Glycerol/0.26 mole Isophthalic Acid/1.03 mole Succinic Acid | 0.1% MTBO (Butyltin hydroxide oxide hydrate) |
| 47 | Poly(Bisphenol A Carbonate) | 9.37% | 0.781 mole Tritan Copolyester/3.992 mole 1,3-Propanediol/2.502 mole Succinic Acid | 0.1% Ti(BuO)4 present in digested intermediate |
| 48 | Poly(Bisphenol A Carbonate) | 9.47% | 0.85 mole PCTA/0.944 mole Neopentyl Glycol/0.765 mole PG/0.114 mole Glycerol/0.313 mole Isopthalic Acid/1.247 mole Succinic Acid | 0.1% MTBO (Butyltin hydroxide oxide hydrate) |
| 49 | Poly(Bisphenol A Carbonate) | 9.04% | 0.469 mole PCTA/1.04 mole CDHM/0.181 mole Terephthalic Acid/0.053 mole Dimer Fatty Acid | 0.1% Ti(BuO)4 present in digested intermediate |

TABLE 2-continued

Physical Characteristics of the Digestion Product from Digestible Polymers

| Polyol Example No. | Acid Value mg KOH/g | OHV (mg KOH/g) | Color | Settling | Clarity | 25° C., Viscosity (cP) at unless noted 50% Torque, unless noted |
|---|---|---|---|---|---|---|
| 1 | 4.0 | 324.0 | Green-amber | None | Opaque | 4535 |
| 2 | 1.2 | 238.3 | Brown-amber | Slight | Semi-transparent | 1836 (50° C.) |
| 3 | 0.4 | 290.8 | Black-amber | Slight | Opaque | 5543 |
| 4 | 0.4 | 120.4 | Brown-amber | Slight | Semi-transparent | 22380 (50° C.) |
| 5 | 0.4 | 322.7 | Black-amber | None | Dark | 8769 |
| 6 | 1.1 | 323.2 | Black-red | None (filtered) | Dark | 7378 |
| 7 | 1.2 | 323.6 | Black-red | None | Dark | 6586 |
| 8 | 2.5 | 356.8 | Amber | None | Transparent | 5745 |
| 9 | 1.4 | 330.7 | Dark brown | None | Opaque | 7483 |
| 10 | 1.3 | 326.6 | Brown | Yes | Opaque | 4649 |
| 11 | 3.5 | 363.3 | Dark amber | Slight | Dark | 6546 |
| 12 | 0.5 | 338.8 | Amber | None | Transparent | 3954 |
| 13 | 0.4 | 255.5 | Amber | None | Transparent | 7013 |
| 14 | 7.7 | 371.1 | Dark red | None | Dark | 6023 |
| 15 | 4.2 | 360.2 | Dark red | None | Dark | 7956 |
| 16 | 0.6 | 309.3 | Dark red | None | Transparent | 7468 |
| 17 | 1.2 | 399.3 | Mustard yellow | None | Opaque | 1023 (100° C.) |
| 18 | 0.3 | 363.2 | Amber | None | Transparent | 2999 |
| 19 | 1.1 | 957.8 | Dark brown | Slight | Opaque | 396.4 |
| 20 | 3.1 | 1000.2 | Dark red-brown | None | Dark | 42 (35% torque) |
| 21 | 1.2 | 321.3 | Dark green | None | Opaque | 8098 |
| 22 | 2.1 | 666.2 | Dark brown/black | None | Dark | 2946 |
| 23 | 2.8 | 336.4 | Dark brown/black | None | Dark | 7113 |
| 24 | 25.7 | 622.1 | Dark brown/black | None | Dark | 3488 |
| 25 | 14.0 | 369.9 | Dark brown/black | None | Dark | 980.2 |
| 26 | 0.7 | 279.1 | red-pink | None | Opaque | 14937 |
| 27 | 2.5 | 472.1 | Dark brown/black | Solidified at room temp. | Dark | — |
| 28 | 6.1 | 333.6 | Dark brown/black | None | Dark | 11767 |
| 29 | 3.1 | 283.6 | Amber/Golden | None | Transparent | 12090 |
| 30 | 2.6 | 345.6 | Dark brown | None | Dark | 10218 |
| 31 | 2.7 | 306.1 | Brown | Slight, Thick at room temp. | Opaque | 10964 |
| 32 | 4.4 | 469.6 | Dark brown/amber | None | Dark | 1825 |
| 33 | 12.0 | 347.3 | Brown | None, Solidified at room temp. | Opaque | 149.7 (125° C.) |
| 34 | 6.4 | 396.7 | Dark brown | None | Dark | 5632 |
| 35 | 4.2 | 259.4 | Dark brown | None, Solidified at room temp. | Opaque | 3023 (150° C.) |
| 36 | 1.1 | 340.2 | Brown | None | Opaque | 14277 |
| 37 | 1.2 | 289.0 | Brown | None | Opaque | 5488 (50° C.) |
| 38 | 7.4 | 220.0 | Orange | None | Transparent | 15207 |
| 39 | 1.4 | 312.4 | Dark yellow | None, Solidified at room temp. | Opaque | 3453 (125° C.) |
| 40 | 2 | 353.7 | Brown | None, After filtration | Opaque | 601 |
| 41 | 1.7 | 228.3 | Brown | None, After filtration | Transparent | 5733 |
| 42 | 4.1 | 134.1 | Dark Amber | None | Transparent | 9000 (100° C.) |
| 43 | 1.9 | 73.6 | White | None | Opaque | 9410 (100° C.) |
| 44 | 1.8 | 93.6 | Green | None | Translucent | 31056 (Cut with Xylene) |
| 45 | 4.2 | 91.2 | Golden | None | Transparent | 5768 (50° C.) |
| 46 | 5 | 75.3 | Green | None | Translucent | — |
| 47 | 4.6 | 202.1 | Yellow-gold | None | Transparent | 17,496 |
| 48 | 3.7 | 36.4 | Green | None | Opaque | — |
| 49 | 3.3 | 255.0 | Light Grey | None | Opaque | — |

TABLE 3

Physical Characteristics of Coatings Made from Digestible Polymers

| Polyol Example No. | Digestible Polymer | Coating Thickness, mil. | Konig Pendulum Hardness, Avg. Oscillations | Konig Pendulum Hardness, Avg. Sec. | Pencil Hardness, Avg. | Adhesion, Avg. | 1 hr. Mustard Resistance | 1 hr. Sunscreen Resistance | 1 hr. Windex Resistance | 1 hr. 100 proof Vodka Resistance | 24 hr. DI Water Resistance | MEK Double Rubs | ⅛" Mandrel Test |
|---|---|---|---|---|---|---|---|---|---|---|---|---|---|
| 5 | Recycled Polyisocyanurate Insulating Foam | 2.27 | 51 | 71.6 | H | 5B | 4 | 5 | 5 | 4 | 5 | 36 | P |
| 6 | Goose Down Feathers | 2.45 | 42 | 58.5 | H | 5B | 4 | 4 | 5 | 3 | 4 | 20 | P |
| 8 | Poly(Bisphenol A | 2.11 | 84 | 118.5 | H | 5B | 5 | 5 | 5 | 5 | 4 | 31 | P |
| 9 | Chitin from Shrimp Shells | 2.21 | 45 | 63.1 | H | 5B | 4 | 5 | 4 | 5 | 5 | 35 | P |
| 12 | Recycled Polylactic Acid Drinking Cups | 2.08 | 63 | 89.0 | H | 5B | 5 | 5 | 5 | 4 | 4 | 29 | F |
| 14 | Soy protein acid hydrolysate | 2.27 | 57 | 79.6 | H | 5B | 4 | 5 | 5 | 3 | 4 | 30 | F |
| 16 | Recycled Polyurethane Foam (UFP Technologies Polyether Black 30 ppi) | 2.21 | 24 | 33.6 | H | 5B | 4 | 4 | 4 | 3 | 4 | 14 | P |
| 17 | Nylon 6 | 2.06 | 61 | 85.4 | H | 5B | 4 | 5 | 5 | 4 | 5 | 68 | P |
| 21 | Recycled Flexible Polyurethane Foam (Carex Health Brands Knee | 2.31 | 57 | 82.4 | H | 5B | 4 | 5 | 5 | 4 | 5 | 72 | P |
| 29 | Poly(Bisphenol A | 1.89 | 109 | 152.7 | H | 5B | 5 | 5 | 5 | 4 | 5 | 5 | F |
| 30 | Zein from Corn | 1.63 | 67 | 94.6 | H | 0B | 5 | 5 | 5 | 4 | 5 | 11 | P |
| 32 | Waste Chicken Feathers | 1.34 | 84 | 117.5 | H | 5B | 4 | 3 | 5 | 1 | 1 | 6 | P |
| 34 | Potato Starch | 1.21 | 134 | 188.8 | 2H | 4.5B | 5 | 5 | 4 | 2 | 5 | 5 | F |
| 37 | Cellulose | 1.54 | 137 | 192.9 | 3H | 5B | 5 | 5 | 5 | 5 | 5 | 73 | F |
| 38 | Poly(Bisphenol A | 1.31 | 9 | 12.1 | H | 0B | 3 | 4 | 5 | 1 | 3 | 9 | P |
| 41 | Pectin | 1.71 | 74 | 104.5 | 3B | 5B | — | 5 | 5 | 5 | 5 | 24.5 | P |
| 42 | Recycled Poly(Bisphenol A Carbonate) (Example XV) | 0.99 | 133 | 186.9 | HB | 5B | — | 5 | 5 | 5 | 5 | 26 | P |
| 43 | Recycled Poly(Bisphenol A Carbonate) (Example XVI) | 1.04 | 126 | 176 | HB | 5B | — | 5 | 5 | 5 | 5 | 33 | F |
| 44 | Recycled Poly(Bbisphenol A Carbonate) (Example XVII) | 0.85 | 115 | 161.5 | B | 5B | — | 5 | 5 | 5 | 5 | 25.5 | P |
| 46 | Recycled Poly(Bisphenol A Carbonate) (Example XIX) | 0.87 | 159 | 223 | HB | 5B | — | 5 | 5 | 5 | 5 | 16 | P |

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as being composed of the components prior to mixing, because upon mixing certain components can further react or be transformed into additional materials.

All percentages and ratios used herein, unless otherwise indicated, are by weight.

What is claimed is:

1. A polyester polyol made by a process comprising:
  (a) heating an aromatic polyacid source selected from a thermoplastic polyester with a glycol to give an intermediate; and
  (b) reacting the resulting intermediate with a digestible polymer selected from polylactic acids, synthetic polyamides, polycarbonates, polyurethanes, polyisocyanurates, polyethers, proteins, polysaccharides, polylactones, and polylactams, or combinations thereof;
  wherein the molar ratio of glycol to aromatic polyacid source is at least 0.8:1, and the polyol has a hydroxyl number within the range of about 10 to about 800 mg KOH/g.

2. The polyester polyol according to claim 1 wherein the thermoplastic polyester is selected from copolymers of
  (a) acids selected from terephathlic acid, 2,5-furandicarboxylic acid, isophthalic acid, dihydroferulic acid, salts thereof, C1-C6 monoesters thereof, C1-C6 diesters thereof, and combinations thereof; and
  (b) diols selected from ethylene glycol, 1,2-propanediol, 1,3-propanediol, 1,2-butanediol, 1,3-butanediol, 1,4-butanediol, 2,3-butanediol, 1,3-cyclohexane diol, 1,4-cyclohexane diol, 1,3-cycohexanedimethanol, 1,4-cyclohexanedimethanol, 2,2,4,4-tetramethyl-1,3-cyclobutane diol, and combinations thereof.

3. The polyester polyol according to claim 1 wherein the thermoplastic polyester is selected from polyethylene terephthalate (PET), polybutylene terephthalate, polytrimethylene terephthalate (PTT), glycol-modified polyethylene terephthalate, copolymers of terephthalic acid and 1,4-cyclohexanedimethanol, isophthalic acid-modified copolymers of terephthalic acid and 1,4-cyclohexanedimethanol, copolymers of 2,5-furandicarboxylic acid or C1-C6-dialkyl 2,5-furandicarboxylates, copolymers of terephthalic acid and 2,2,4,4-tetramethyl-1,3-cyclobutane diol, and combinations thereof.

4. The polyester polyol according to claim 1 wherein the glycol is selected from ethylene glycol, propylene glycol, 1,3-propanediol, 1,2-butylene glycol, 1,3-butylene glycol, 1,4-butanediol, 2-methyl-1,3-propanediol, neopentyl glycol, glycerol, trimethylolpropane, 3-methyl-1,5-pentanediol, 1,4-cyclohexanedimethanol, diethylene glycol, tetraethylene glycol, dipropylene glycol, triethylene glycol, tripropylene glycol, polyethylene glycol, polypropylene glycol, erythritol, pentaerythritol, sorbitol, and block or random copolymer glycols of ethylene oxide and propylene oxide, or combinations thereof.

5. The polyester polyol according to claim 1 having a hydroxyl number within the range of about 25 to about 500 mg KOH/g.

6. The polyester polyol according to claim 1 wherein the weight percent of digestible polymer incorporated into the polyester polyol is from 1% to 75% by weight of the polyester polyol.

7. The polyester polyol according to claim 1 wherein the aromatic polyacid source and glycol are heated at a temperature within the range of about 80° C. to about 260° C.

8. The polyester polyol according to claim 1 having an acid number of less than 10 mg KOH/g.

9. The polyester polyol according to claim 1 wherein the polycarbonate is poly(bisphenol A carbonate).

10. A polyester polyol according to claim 1 having a viscosity at 25° C. less than about 20,000 cP.

11. A polyester polyol according to claim 1 having a recycle content greater than 50 weight %, as calculated by summing the masses of any recycled thermoplastic polyester, recycled glycol, and recycled digestible polymer, dividing this sum by the total mass of the thermoplastic polyester, glycol, and digestible polymer, and multiplying the result by 100.

12. A polyurethane made from the polyester polyol according to claim 1.

13. A polyurethane comprising a polyester polyol according to claim 1.

14. A coating made from the polyester polyol according to claim 1.

15. A coating comprising a polyester polyol according to claim 1.

16. A polymeric foam made from the polyester polyol according to claim 1.

17. A polymeric foam comprising a polyester polyol according to claim 1.

18. A mono-acrylate, di-acrylate, polyacrylate, monomethacrylate, dimethacrylate, polymethacrylate, urethane acrylate, or urethane methacrylate made from the polyester polyol according to claim 1.

19. A mono-acrylate, di-acrylate, polyacrylate, monomethacrylate, dimethacrylate, polymethacrylate, urethane acrylate, or urethane methacrylate comprising a polyester polyol according to claim 1.

20. A polyester polyol made by a process comprising reacting an aromatic polyacid source selected from a thermoplastic polyester, a glycol, and a digestible polymer selected from polylactic acids, synthetic polyamides, polycarbonates, polyurethanes, polyisocyanurates, polyethers, proteins, polysaccharides, polylactones, and polylactams, or combinations thereof; wherein the molar ratio of glycol to aromatic polyacid source is at least 1.0:1, and the polyester polyol has a hydroxyl number within the range of about 10 to about 800 mg KOH/g.

21. A polyester polyol comprising recurring units made by a process comprising reacting an intermediate and a digestible polymer:
  (a) wherein the intermediate is made by heating an aromatic polyacid source selected from a thermoplastic polyester and a glycol, and
  (b) the digestible polymer is selected from polylactic acids, synthetic polyamides, polycarbonates, polyurethanes, polyisocyanurates, polyethers, proteins, polysaccharides, polylactones, and polylactams, or combinations thereof.

22. A polyester polyol according to claim 21 further comprising recurring units of a hydrophobe or nonionic surfactant, or combinations thereof.

23. A polyester polyol according to claim 22 wherein the hydrophobe or nonionic surfactant is selected from ricinoleic acid, castor oil, ethoxylated castor oil, saturated or unsaturated $C_9$-$C_{18}$ dicarboxylic acids, vegetable oils, fatty acids, fatty acid esters, modified vegetable oils, fatty triglycerides, cardanol, derivatives of cardanol, recycled cooking oil, isostearyl alcohol, hydroxy-functional materials derived from epoxidized, ozonized, or hydroformylated fatty esters, dimer fatty acids, block copolymers of ethylene oxide with propylene oxide, alkoxylated alkyl phenols, alkoxylated fatty alcohols, or combinations thereof.

24. A process for making a polyester polyol comprising reacting an aromatic polyacid source selected from a thermoplastic polyester, a glycol, and a digestible polymer selected from polylactic acids, synthetic polyamides, polycarbonates, polyurethanes, polyisocyanurates, polyethers, proteins, polysaccharides, polylactones, and polylactams, or combinations thereof; wherein the molar ratio of glycol to aromatic polyacid group is at least 0.8:1, and the polyester polyol has a hydroxyl number within the range of about 10 to about 800 mg KOH/g.

25. A process for making a polyester polyol comprising:
(a) heating an aromatic polyacid source selected from a thermoplastic polyester with a glycol to give an intermediate; and
(b) reacting the resulting intermediate with a digestible polymer selected from polylactic acids, synthetic polyamides, polycarbonates, polyurethanes, polyisocyanurates, polyethers, proteins, polysaccharides, polylactones, and polylactams, or combinations thereof;
wherein the molar ratio of glycol to aromatic polyacid source is at least 0.8:1, and the polyester polyol has a hydroxyl number within the range of about 10 to about 800 mg KOH/g.

26. A polyester polyol comprising recurring units made by a process comprising reacting an intermediate and a digestible polymer wherein,
(a) the intermediate is made by heating (i) an aromatic polyacid source selected from terephthalic acid, isophthalic acid, and orthophthalic acid, or esters or anhydrides thereof, or combinations of said acids, esters, or anhydrides thereof, and (ii) a glycol; and
(b) the digestible polymer is selected from polylactic acids, synthetic polyamides, polycarbonates, polyurethanes, proteins, polysaccharides, polylactones, and polylactams, or combinations thereof.

27. A polyester polyol comprising recurring units made by a process comprising reacting an intermediate and a digestible polymer wherein,
(a) the intermediate is made by heating (i) an aromatic polyacid source selected from terephthalic acid, isophthalic acid, or esters thereof, or combinations of said acids or esters thereof, and (ii) a glycol; and
(b) the digestible polymer is selected from polylactic acids, synthetic polyamides, polycarbonates, polyurethanes, polyisocyanurates, proteins, polysaccharides, polylactones, and polylactams, or combinations thereof.

* * * * *